(12) United States Patent
Zhang

(10) Patent No.: US 8,053,577 B2
(45) Date of Patent: Nov. 8, 2011

(54) DERIVATIVES OF 5,9-METHANOCYCLOOCTA[B]PYRIDIN-2-(1H)-ONE, THEIR PREPARATION AND USE AS ANALGESICS

(76) Inventor: Hesheng Zhang, Tianjin (CN)

( * ) Notice: Subject to any disclaimer, the term of this patent is extended or adjusted under 35 U.S.C. 154(b) by 495 days.

(21) Appl. No.: 12/324,949

(22) Filed: Nov. 28, 2008

(65) Prior Publication Data

US 2009/0118320 A1    May 7, 2009

Related U.S. Application Data

(63) Continuation of application No. PCT/CN2007/001919, filed on Jun. 19, 2007.

(30) Foreign Application Priority Data

Jul. 5, 2006  (CN) .............................. 200610014691
Jun. 19, 2007  (CN) .............................. 200710101787

(51) Int. Cl.
  *C07B 221/22*   (2006.01)
  *A61K 31/439*   (2006.01)

(52) U.S. Cl. ......................................... 546/93; 514/295
(58) Field of Classification Search .................... 546/93; 514/295
  See application file for complete search history.

(56) References Cited

U.S. PATENT DOCUMENTS

RE38,460 E * 3/2004 Zhu et al. ...................... 514/295
* cited by examiner

*Primary Examiner* — Robert Havlin
(74) *Attorney, Agent, or Firm* — Matthias Scholl P.C.; Matthias Scholl

(57) ABSTRACT

A compound of Formula I, a pharmaceutically-acceptable salt or a hydrate thereof, wherein $R^1$ is H, or $C_{1-4}$ alkyl; $R^2$ is H, halogen, or $C_{1-4}$ alkyl; $R^3$ is H, halogen, or $C_{1-4}$ alkyl, and $R^4$ is $C_{1-6}$ alkyl, aryl; or $=CR^3R^4$ is cyclopentylidene, cyclohexylidene, 1-methylpiperidin-4-ylidene, or inden-1-ylidene; $R^5$ is independently at each occurrence F, Cl, Br, $CF_3$, $R^9$, $OR^9$, $NR^9R^{10}$, $NO_2$, CN, $COOR^9$, $O_2CR^9$, $CONR^9R^{10}$, $NR^9C(O)R^{10}$, heterocyclic group, aryl, or a group of Formula II; $R^6$ is H, halogen, or $C_{1-4}$ alkyl; $R^7$ is H, halogen, or $C_{1-4}$ alkyl; $R^8$ is H, $C_{1-4}$ alkyl group; $R^9$ is H, or $C_{1-6}$ alkyl; $R^{10}$ is H, or $C_{1-6}$ alkyl; $R^{11}$ is H, or $C_{1-4}$ alkyl; $R^{12}$ is H, or $C_{1-4}$ alkyl; m is 0, 1, or 2; when $R^5$ is F, Cl, Br, $CF_3$, $R^9$, $OR^9$, $NR^9R^{10}$, $NO_2$, CN, $COOR^9$, $O_2CR^9$, $CONR^9R^{10}$, $NR^9C(O)R^{10}$, heterocyclic group, or aryl, n is 1, 2, 3, or 4; when $R^5$ is the group of Formula II, n is 0, 1, 2, 3, or 4; x is 0, 1, 2, 3, or 4.

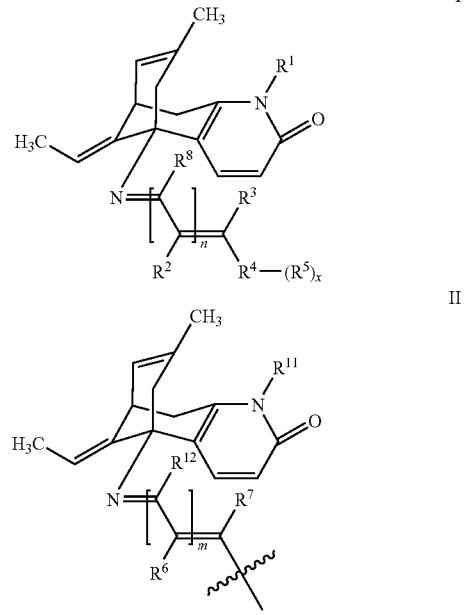

17 Claims, 1 Drawing Sheet

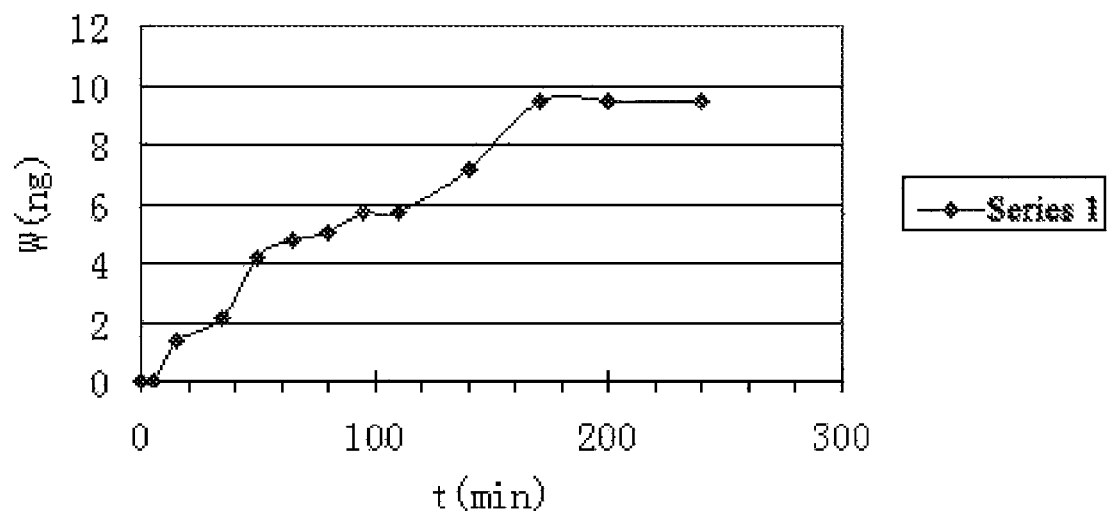

DERIVATIVES OF 5,9-METHANOCYCLOOCTA[B]PYRIDIN-2-(1H)-ONE, THEIR PREPARATION AND USE AS ANALGESICS

CROSS-REFERENCE TO RELATED APPLICATIONS

This application is a continuation of International Patent Application No. PCT/CN2007/001919, with an international filing date of Jun. 19, 2007, designating the United States, now pending, which is based on China Patent Application No. 200610014691.6, filed Jul. 5, 2006, and China Patent Application No. 200710101787.0 filed on Jun. 19, 2007. The contents of all of these specifications, including any intervening amendments thereto, are incorporated herein by reference.

BACKGROUND OF THE INVENTION

1. Field of the Invention

The invention relates to analgesic 5,9-methanocycloocta[b]pyridin-2(1H)-one derivatives, their preparation, and use as analgesic agents.

2. Description of the Related Art

Pain is a typical sensory experience that may be described as the unpleasant awareness of a noxious stimulus or bodily harm. Individuals experience pain by various daily hurts and aches, and occasionally through more serious injuries or illnesses. For example, pain may be caused by neurothlipsis or nervous lesions due to the expansion of cancer cells in cancer patients, by damage of human tissues or organs, by autoimmune reaction such as inflammation (arthritis, gastritis, or hepatitis), or by abnormities in the central nervous system (brain tissues).

Pain of any type is the most frequent reason for physician consultation in the United States, prompting over half of all Americans to seek medical care annually and causing heavy economic losses to society. Pain management is one of the most common means of symptomatic treatments, and virtually the only focus in late stages of terminal illnesses, such as incurable cancer.

Conventional analgesics include two main types: opiate receptor ligands, with the typical example of morphine, which has strong analgesic effects but is prone to cause addiction; and non-narcotic analgesics, with the typical example of aspirin-derived paracetamol. With multiple mechanisms of action and conceived and manufactured successfully via modern processes of drug design, screening and development, this type of drugs have weak analgesic effects, but they seldom forming dependence. Although some of these analgesics have other serious side effects, e.g., they may cause damage to the digestive tract, they are widely used and have an estimated combined market share of nearly 10 billion US dollars.

Acetylcholine was the first neurotransmitter to be discovered. However, there has been hardly any research in the area of acetylcholine receptors (AcChR) and acetylcholinesterase as analgesic targets. Nevertheless, in European Pat. No. EP 413667 A and U.S. Pat. No. 5,010,083, compounds used for treatment of both memory loss and relief of pain have been reported, which suggests that improvement of memory has some association with analgesia, and further reveals that increase in the level of acetylcholine may have analgesic action.

In addition, Stoyan once reported that the alkaloids nivalin and syntostigmine could alleviate migraine pain (Stoyan, Archives Suisses de Neurologie, Neurochirurgie et de Psychiatrie, 1968, 102, pp. 299-312). It was later found that these two compounds could inhibit the activity of acetylcholine esterase. Because of a low inhibition activity of acetylcholine esterase or a low ability to permeate the blood-brain barrier, higher doses of these two compounds, and other acetylcholine esterase inhibitors subsequently tested, are required in order to provide therapeutic effects.

To achieve high concentrations, these compounds must be administered by injection. Hence, on one hand, the blood drug concentration is so high so as to have many side effects; on the other hand, the administration by injection is inconvenient. As a result, the research on acetylcholine esterase inhibitors used for treatment of migraine was put on hold. This was the first time when it was proposed that acetylcholine esterase inhibitors could be used for treatment of migraine.

The breakthrough in this field came from research and development of novel inhibitors of acetylcholine esterase. These novel inhibitors, such as donepezil, have high activity, highly-selectivity and high permeability through the blood-brain barrier, so that they are able to overcome the shortcomings of the first generation of acetylcholine esterase inhibitors described above for the treatment of migraine. As disclosed in U.S. Pat. No. 6,608,088, donepezil was observed to have efficacy on migraine in clinical trials.

Huperzine A can inhibit acetylcholine esterase (ACHE) selectively, has high activity, and is easy to penetrate blood-brain-barrier and spinal-fluid-barrier. In addition huperzine A has effects on improvement of memory reappearance and enhancement of memory retention. Recently, we have found that Huperzine A and derivatives thereof have strong analgesic effects (Chinese Pat. Appl. 200510014685.6), and curative effect on migraine. However, Huperzine A has certain drawbacks, such as high toxicity, low therapeutic index (TI), narrow window between maximum tolerance dose and curative dose (CD).

BRIEF SUMMARY OF THE INVENTION

In view of the above-described problems, this invention relates to a series of analgesic 5,9-methanocycloocta[b]pyridin-2(H)-one derivatives. Through animal toxicology study and animal analgesic pharmacodynamics experiments, we found that 5,9-methanocycloocta[b]pyridin-2(H)-one derivatives possess high analgesic effects, and long drug efficacy time. More importantly, 5,9-methanocycloocta[b]pyridin-2(H)-one derivatives have much lower toxicity than Huperzine A. Consequently, compared to Huperzine A, they are safer, more effective, and more convenient analgesics.

In one embodiment of the invention, provided is a compound of Formula I,

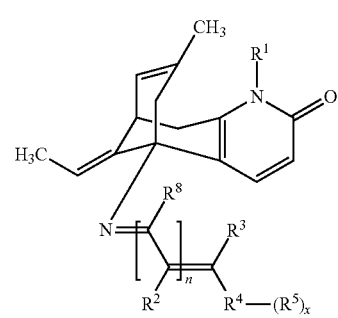

a pharmaceutically-acceptable salt, or a hydrate thereof, which is useful in the treatment of pain, functional pain syndrome, or organogenic pain syndrome; wherein $R^1$ is H, or $C_{1-4}$ alkyl; $R^2$ is H, halogen, or $C_{1-4}$ alkyl; $R^3$ is H, halogen, or $C_{1-4}$ alkyl, and $R^4$ is $C_{1-6}$ alkyl, aryl; or $=CR^3R^4$ is cyclopentylidene, cyclohexylidene, 1-methylpiperidin-4-ylidene, or inden-1-ylidene; $R^5$ is independently at each occurrence F, Cl, Br, $CF_3$, $R^9$, $OR^9$, $NR^9R^{10}$, $NO_2$, CN, $COOR^9$, $O_2CR^9$, $CONR^9R$, $NR^9C(O)R^{10}$, heterocyclic group, aryl, or a group of Formula II

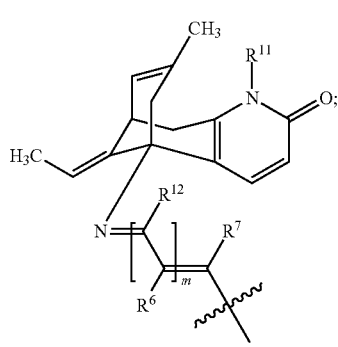

$R^6$ is H, halogen, or $C_{1-4}$ alkyl; $R^7$ is H, halogen, or $C_{1-4}$ alkyl; $R^8$ is H, $C_{1-4}$ alkyl group; $R^9$ is H, or $C_{1-6}$ alkyl; $R^{10}$ is H, or $C_{1-6}$ alkyl; $R^{11}$ is H, or $C_{1-4}$ alkyl; $R^{12}$ is H, or $C_{1-4}$ alkyl; m is 0, 1, or 2; when $R^5$ is F, Cl, Br, $CF_3$, $R^9$, $OR^9$, $NR^9R^{10}$, $NO_2$, CN, $COOR^9$, $O_2CR^9$, $CONR^9R^{10}$, $NR^9C(O)R^{10}$, heterocyclic group, or aryl, n is 1, 2, 3, or 4; when $R^5$ is the group of Formula II, n is 0, 1, 2, 3, or 4; x is 0, 1, 2, 3, or 4.

The above $C_{1-4}$ alkyl, $C_{1-6}$ alkyl may be linear chain alkyl, branched chain or cyclo alkyl group, saturated or unsaturated alkyl group, and may be optionally substituted with one or more F, Cl, OH, $C_{1-4}$ alkoxy, $C(O)OC_{1-4}$ alkyl, $NH_2$, $NH(C_{1-4}$ alkyl), $N(C_{1-4}$ alkyl$)_2$, $C(O)NH_2$, $C(O)NHC_{1-4}$ alkyl, $C(O)N(C_{1-4}$ alkyl$)_2$, COOH, phenyl or substituted phenyl.

Cyclopentylidene, cyclohexylidene, 1-methylpiperidin-4-ylidene, inden-1-ylidene may be optionally substituted with one or more F, Cl, OH, $C_{1-4}$ alkoxy, $C(O)OC_{1-4}$ alkyl, $NH_2$, $NH(C_{1-4}$ alkyl), $N(C_{1-4}$ alkyl$)_2$, $C(O)NH_2$, $C(O)NHC_{1-4}$ alkyl, $C(O)N(C_{1-4}$ alkyl$)_2$, COOH, phenyl, or substituted phenyl.

Aryl may be a five-membered ring or a six-membered ring, and maybe a single ring or two or three fused rings; it may contain 1, 2, or 3 O, N, S atoms and may be substituted with one or more F, OH, $C_{1-4}$ alkoxy, $COOC_{1-4}$ alkyl, $NH_2$, $NH(C_{1-4}$ alkyl), $N(C_{1-4}$ alkyl$)_2$, $C(O)NH_2$, $C(O)NHC_{1-4}$ alkyl, $C(O)N(C_{1-4}$ alkyl$)_2$, COOH.

When there are two or more $R^9$ in Formula I, they may be the same or different substituents.

When there are two or more $R^{10}$ in Formula I, they may be the same or different substituents.

The analgesic effect with a single dose of the compounds represented by Formula I is preliminarily screened at single time point through hot-plate test, with fortanodyn and aspirin as positive controls. All of the compounds are administered intragastrically. The results are summarized in Table 3. The data in Table 3 suggests that all of the compounds of Formula I should have analgesic effects.

On the basis of preliminary screening results, several representative compounds were selected to test their analgesic duration, and a part of the results is listed in Table 4. The results illustrate that the analgesic duration of most compounds is longer than 2 hours after a single oral administration, and that some of the compounds have analgesic duration lasting longer than 4 hours. Statistical treatment of results shows that all the tested compounds have significant analgesic effects ($P<0.05$).

Furthermore, the dose-effect relationship on an analgesic model of two compounds was tested and the results are shown in Table 5. Both of the compounds exhibit dose-effect relationship, indicating that the analgesic effect may come from the pharmacological action (AcE inhibition) that was postulated.

This invention relates to the compound of Formula I, pharmaceutically acceptable inorganic salt, organic salt, hydrate, solvate, or crystal form thereof used to treat pain, functional pain syndrome, organogenic pain syndrome, or tissue pain syndrome.

The suitable dose of this type of compounds is between 0.001 and 500 mg; particularly between 0.01 and 100 mg; and more particularly between 0.05 and 50 mg.

The compounds depicted herein are derived from of huperzine A, the (−)-enantiomer. However, the invention is not limited to particular isomers only. Particularly, the compounds of the invention may be pure isomers or a mixture of various isomers.

The compounds of Formula I suitable as active ingredients of drugs to treat pain, functional pain syndrome, organogenic pain syndrome, or tissue pain syndrome comprise compounds wherein $R^1$ is H, methyl, ethyl, propyl, isopropyl or butyl; and particularly wherein $R^1$ is H.

The compounds of Formula I suitable as active ingredients of drugs to treat pain, functional pain syndrome, organogenic pain syndrome, or tissue pain syndrome comprise compounds wherein $R^2$ is H, chloro, bromo, methyl, ethyl, propyl, isopropyl, or butyl; particularly wherein $R^2$ is H, chloro, methyl, or ethyl; and more particularly wherein $R^2$ is H, fluoro, chloro, methyl, or trifluoromethyl.

The compounds of Formula I suitable as active ingredients of drugs to treat pain, functional pain syndrome, organogenic pain syndrome, or tissue pain syndrome comprise compounds wherein $R^3$ is H, fluoro, chloro, methyl, ethyl, propyl, isopropyl, n-butyl, isobutyl, difluoromethyl, or trifluoromethyl; particularly wherein $R^3$ is H, fluoro, chloro, or methyl; and more particularly wherein $R^3$ is H, fluoro, or methyl.

The compounds of Formula I suitable for treating pain, functional pain syndrome, organogenic pain syndrome, or tissue pain syndrome comprise compounds wherein $=CR^3R^4$ is cyclopentylidene, cyclohexylidene, 1-methylpiperidin-4-ylidene, or inden-1-ylidene.

The compounds of Formula I suitable for treating pain, functional pain syndrome, organogenic pain syndrome, or tissue pain syndrome comprise compounds wherein $R^4$ is methyl, ethyl, propyl, or isopropyl.

The compounds of Formula I suitable for treating pain, functional pain syndrome, organogenic pain syndrome, or tissue pain syndrome comprise compounds wherein aryl is phenyl, naphthalenyl, anthracenyl, pyridinyl, furanyl, indolyl, thienyl, or pyrrolyl.

The compound of Formula I suitable for treating pain, functional pain syndrome, organogenic pain syndrome, or tissue pain syndrome comprise compounds wherein $R^5$ is F, Cl, Br, $CF_3$, methyl, ethyl, propyl, OH, methoxyl, ethoxyl, propoxyl, $NH_2$, methylamino, ethylamino, propylamino, dimethylamino, diethylamino, dipropylamino, $NO_2$, CN, COOMe, COOEt, $O_2$CMe, $CONH_2$, CONHMe, $CONMe_2$, NHC(O)Me, NHC(O)H, N(Me)C(O)Me, N(Me)C(O)H, $O_2$CH, COOH, or the group of Formula II,

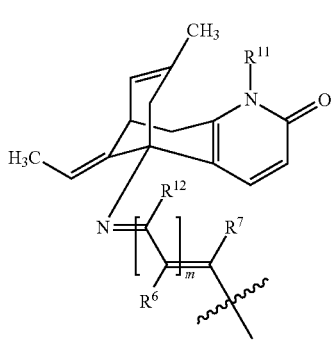

wherein $R^6$ and $R^7$ represent independently H, Me, or Cl; $R^{11}$ and $R^{12}$ are H; m is 0, 1, 2.

The compound of Formula I suitable for treating pain, functional pain syndrome, organogenic pain syndrome, or tissue pain syndrome comprise compounds wherein $R^8$ is H.

The compounds of Formula I suitable for treating pain, functional pain syndrome, organogenic pain syndrome, or tissue pain syndrome comprise, but are not limited to, the following compounds:

1) (5R,9R,11E)-5-(3-phenylprop-2-en-1-ylideneamino)-11-ethylidene-5,6,9,10-tetrahydro-7-methyl-5,9-methanocycloocta[b]pyridin-2(1H)-one:

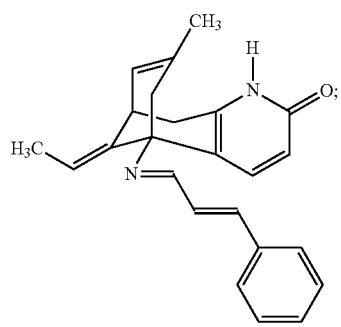

2) (5R,9R,11E)-5-(3-(4-methylphenyl)prop-2-en-1-ylideneamino)-11-ethylidene-5,6,9,10-tetrahydro-7-methyl-5,9-methanocycloocta[b]pyridin-2(1H)-one:

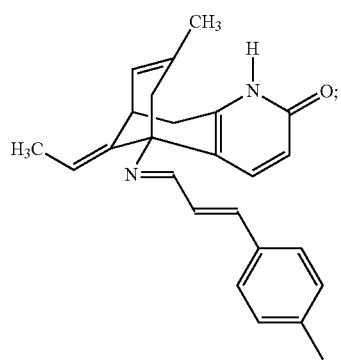

3) (5R,9R,11E)-5-(3-(2-methylphenyl)prop-2-en-1-ylideneamino)-11-ethylidene-5,6,9,10-tetrahydro-7-methyl-5,9-methanocycloocta[b]pyridin-2(1H)-one:

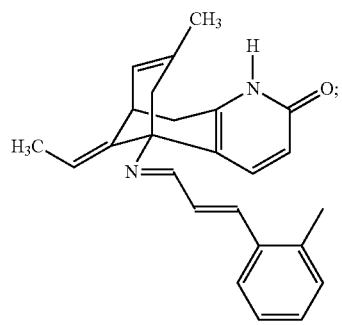

4) (5R,9R,11E)-5-(3-(3-methylphenyl)prop-2-en-1-ylideneamino)-11-ethylidene-5,6,9,10-tetrahydro-7-methyl-5,9-methanocycloocta[b]pyridin-2(1H)-one:

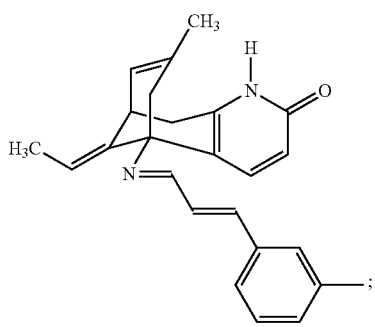

5) (5R,9R,11E)-5-(3-(4-methoxylphenyl)prop-2-en-1-ylideneamino)-11-ethylidene-5,6,9,10-tetrahydro-7-methyl-5,9-methanocycloocta[b]pyridin-2(1H)-one:

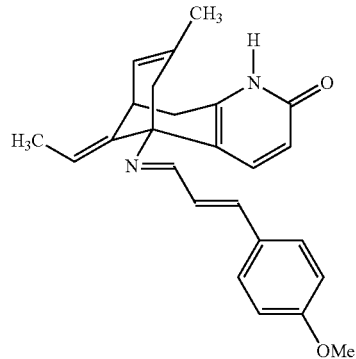

6) (5R,9R,11E)-5-(3-(2-methoxylphenyl)prop-2-en-1-ylideneamino)-11-ethylidene-5,6,9,10-tetrahydro-7-methyl-5,9-methanocycloocta[b]pyridin-2(1H)-one:

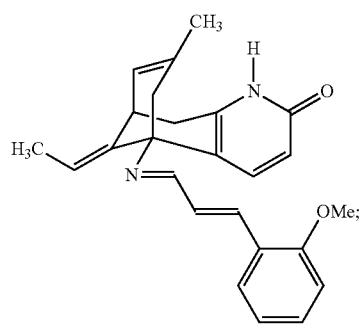

7) (5R,9R,11E)-5-(3-(3-methoxylphenyl)prop-2-en-1-ylideneamino)-11-ethylidene-5,6,9,10-tetrahydro-7-methyl-5,9-methanocycloocta[b]pyridin-2(1H)-one:

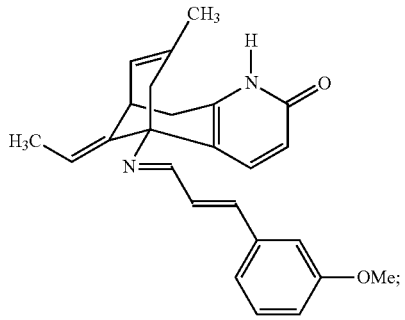

8) (5R,9R,11E)-5-(3-(2-chlorophenyl)prop-2-en-1-ylideneamino)-11-ethylidene-5,6,9,10-tetrahydro-7-methyl-5,9-methanocycloocta[b]pyridin-2(1H)-one:

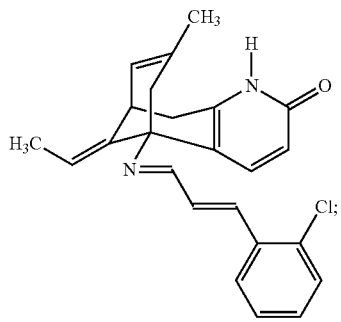

9) (5R,9R,11E)-5-(3-(3-chlorophenyl)prop-2-en-1-ylideneamino)-11-ethylidene-5,6,9,10-tetrahydro-7-methyl-5,9-methanocycloocta[b]pyridin-2(1H)-one:

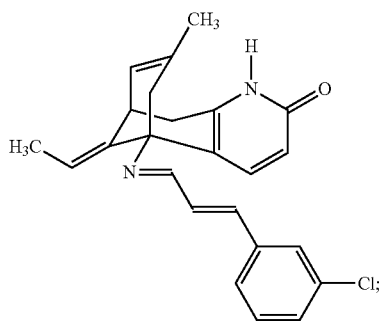

10) (5R,9R,11E)-5-(3-(4-chlorophenyl)prop-2-en-1-ylideneamino)-11-ethylidene-5,6,9,10-tetrahydro-7-methyl-5,9-methanocycloocta[b]pyridin-2(1H)-one:

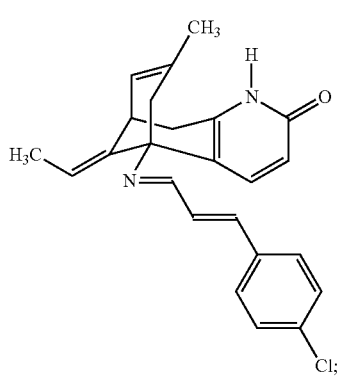

11) (5R,9R,11E)-5-(3-(2-bromophenyl)prop-2-en-1-ylideneamino)-11-ethylidene-5,6,9,10-tetrahydro-7-methyl-5,9-methanocycloocta[b]pyridin-2(1H)-one:

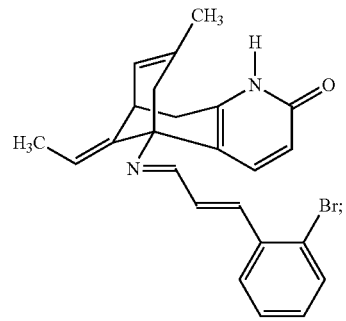

12) (5R,9R,11E)-5-(3-(3-bromophenyl)prop-2-en-1-ylideneamino)-11-ethylidene-5,6,9,10-tetrahydro-7-methyl-5,9-methanocycloocta[b]pyridin-2(1H)-one:

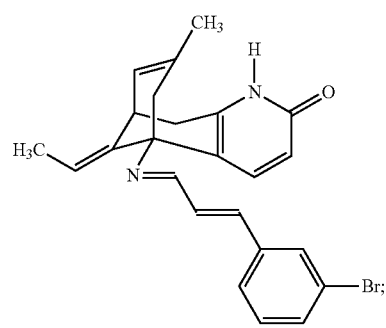

13) (5R,9R,11E)-5-(3-(4-bromophenyl)prop-2-en-1-ylideneamino)-11-ethylidene-5,6,9,10-tetrahydro-7-methyl-5,9-methanocycloocta[b]pyridin-2(1H)-one:

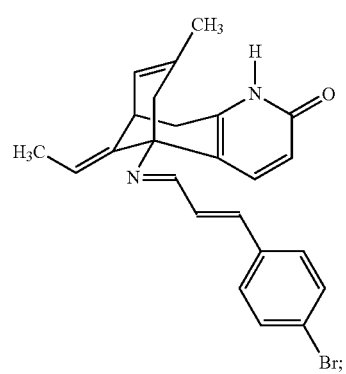

14) (5R,9R,11E)-5-(3-(2-ethylphenyl)prop-2-en-1-ylideneamino)-11-ethylidene-5,6,9,10-tetrahydro-7-methyl-5,9-methanocycloocta[b]pyridin-2(1H)-one:

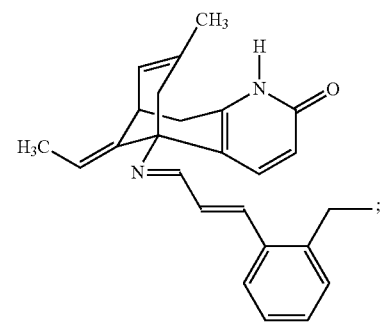

15) (5R,9R,11E)-5-(3-(3-ethylphenyl)prop-2-en-1-ylideneamino)-11-ethylidene-5,6,9,10-tetrahydro-7-methyl-5,9-methanocycloocta[b]pyridin-2(1H)-one:

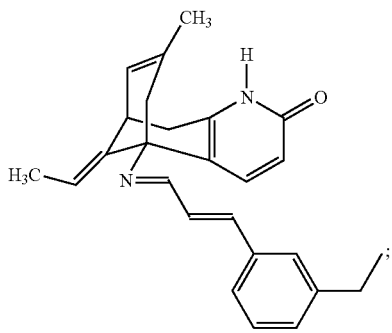

16) (5R,9R,11E)-5-(3-(4-ethylphenyl)prop-2-en-1-ylideneamino)-11-ethylidene-5,6,9,10-tetrahydro-7-methyl-5,9-methanocycloocta[b]pyridin-2(1H)-one:

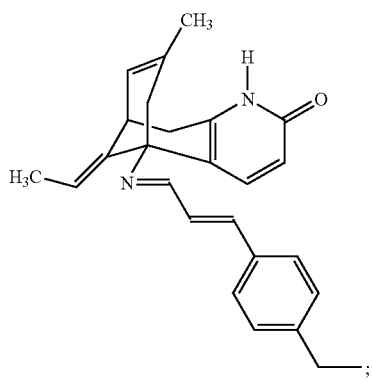

17) (5R,9R,11E)-5-(3-(2-propylphenyl)prop-2-en-1-ylideneamino)-11-ethylidene-5,6,9,10-tetrahydro-7-methyl-5,9-methanocycloocta[b]pyridin-2(1H)-one:

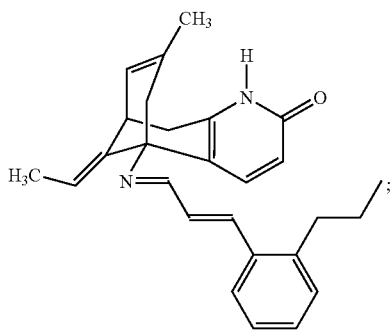

18) (5R,9R,11E)-5-(3-(3-propylphenyl)prop-2-en-1-ylideneamino)-11-ethylidene-5,6,9,10-tetrahydro-7-methyl-5,9-methanocycloocta[b]pyridin-2(1H)-one:

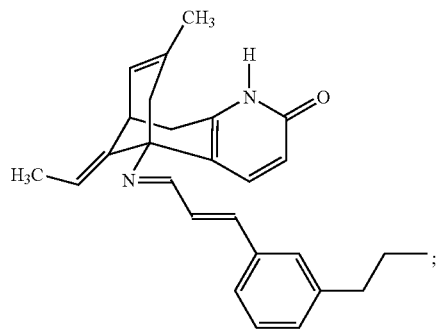

19) (5R,9R,11E)-5-(3-(4-propylphenyl)prop-2-en-1-ylideneamino)-11-ethylidene-5,6,9,10-tetrahydro-7-methyl-5,9-methanocycloocta[b]pyridin-2(1H)-one:

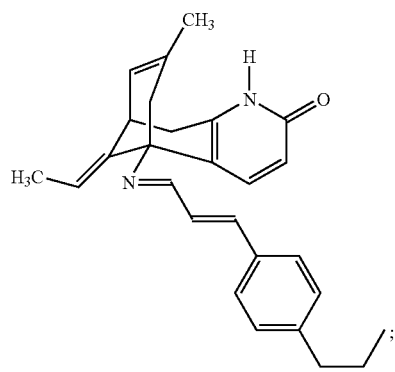

20) (5R,9R,11E)-5-(3-(2-isopropylphenyl)prop-2-en-1-ylideneamino)-11-ethylidene-5,6,9,10-tetrahydro-7-methyl-5,9-methanocycloocta[b]pyridin-2(1H)-one:

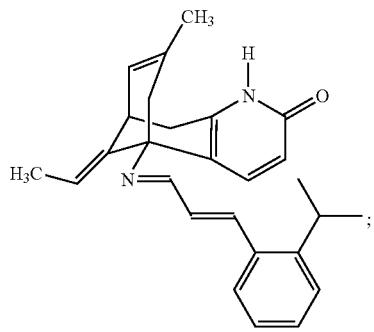

21) (5R,9R,11E)-5-(3-(3-isopropylphenyl)prop-2-en-1-ylideneamino)-11-ethylidene-5,6,9,10-tetrahydro-7-methyl-5,9-methanocycloocta[b]pyridin-2(1H)-one:

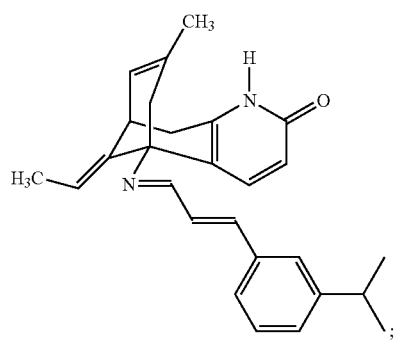

22) (5R,9R,11E)-5-(3-(4-isopropylphenyl)prop-2-en-1-ylideneamino)-11-ethylidene-5,6,9,10-tetrahydro-7-methyl-5,9-methanocycloocta[b]pyridin-2(1H)-one:

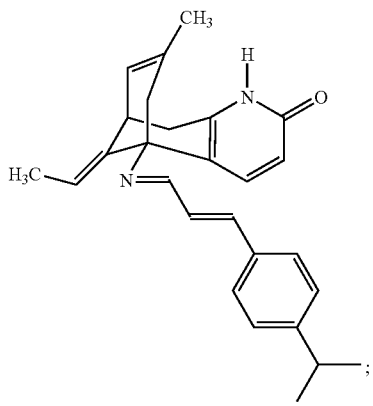

23) (5R,9R,11E)-5-(3-(naphthalen-2-yl)prop-2-en-1-ylideneamino)-11-ethylidene-5,6,9,10-tetrahydro-7-methyl-5,9-methanocycloocta[b]pyridin-2(1H)-one:

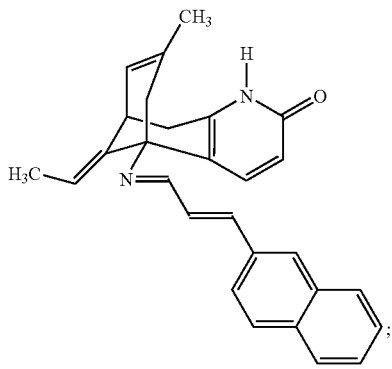

24) (5R,9R,11E)-5-(3-(naphthalen-1-yl)prop-2-en-1-ylideneamino)-11-ethylidene-5,6,9,10-tetrahydro-7-methyl-5,9-methanocycloocta[b]pyridin-2(1H)-one:

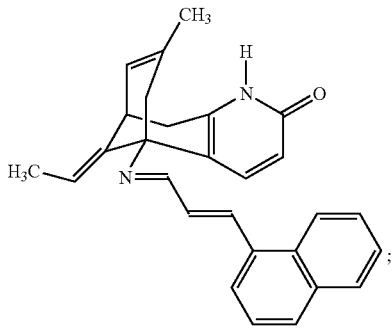

25) (5R,9R,11E)-5-(3-(furan-2-yl)prop-2-en-1-ylideneamino)-11-ethylidene-5,6,9,10-tetrahydro-7-methyl-5,9-methanocycloocta[b]pyridin-2(1H)-one:

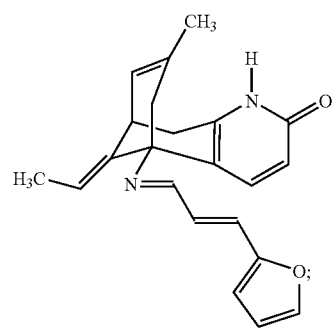

26) (5R,9R,11E)-5-(3-(2-dimethylaminophenyl)prop-2-en-1-ylideneamino)-11-ethylidene-5,6,9,10-tetrahydro-7-methyl-5,9-methanocycloocta[b]pyridin-2(1H)-one:

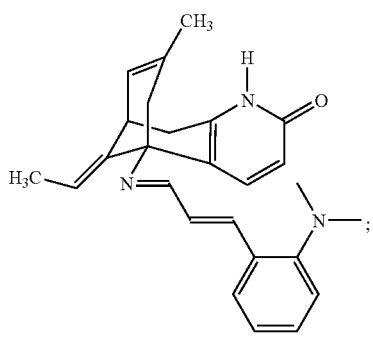

27) (5R,9R,11E)-5-(3-(3-dimethylaminophenyl)prop-2-en-1-ylideneamino)-11-ethylidene-5,6,9,10-tetrahydro-7-methyl-5,9-methanocycloocta[b]pyridin-2(1H)-one:

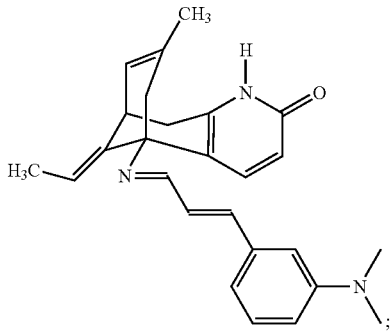

28) (5R,9R,11E)-5-(3-(4-dimethylaminophenyl)prop-2-en-1-ylideneamino)-11-ethylidene-5,6,9,10-tetrahydro-7-methyl-5,9-methanocycloocta[b]pyridin-2(1H)-one:

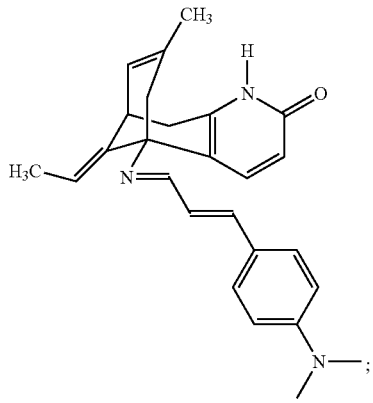

29) (5R,9R,11E)-5-(3-(3,4-dimethoxylphenyl)prop-2-en-1-ylideneamino)-11-ethylidene-5,6,9,10-tetrahydro-7-methyl-5,9-methanocycloocta[b]pyridin-2(1H)-one:

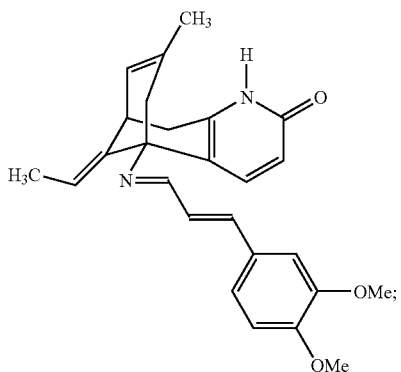

30) (5R,9R,11E)-5-(3-(1H-indol-3-yl)prop-2-en-1-ylideneamino)-11-ethylidene-5,6,9,10-tetrahydro-7-methyl-5,9-methanocycloocta[b]pyridin-2(1H)-one:

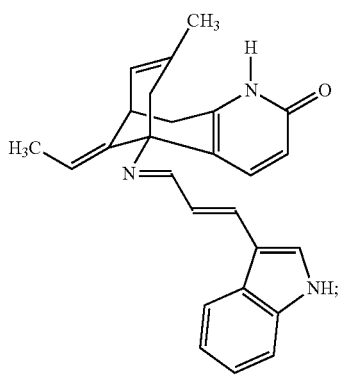

31) (5R,9R,11E)-5-(3-(pyridin-4-yl)prop-2-en-1-ylideneamino)-11-ethylidene-5,6,9,10-tetrahydro-7-methyl-5,9-methanocycloocta[b]pyridin-2(1H)-one:

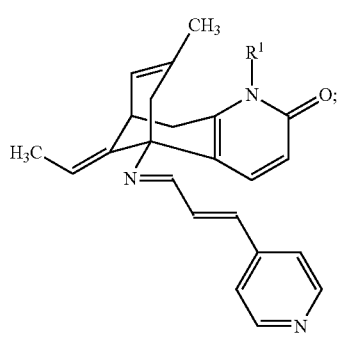

32) (5R,9R,11E)-5-(3-(pyridin-2-yl)prop-2-en-1-ylideneamino)-11-ethylidene-5,6,9,10-tetrahydro-7-methyl-5,9-methanocycloocta[b]pyridin-2(1H)-one:

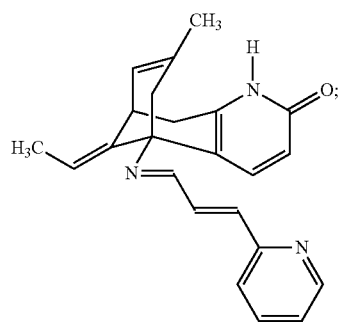

33) (5R,9R,11E)-5-(3-(pyridin-3-yl)prop-2-en-1-ylideneamino)-11-ethylidene-5,6,9,10-tetrahydro-7-methyl-5,9-methanocycloocta[b]pyridin-2(1H)-one:

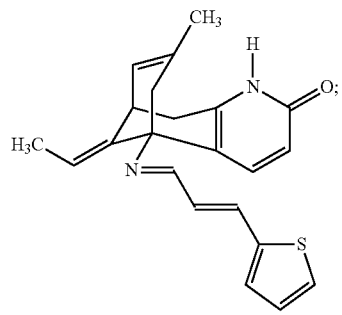

34) (5R,9R,11E)-5-(3-(thiophen-2-yl)prop-2-en-1-ylideneamino)-11-ethylidene-5,6,9,10-tetrahydro-7-methyl-5,9-methanocycloocta[b]pyridin-2(1H)-one:

35) (5R,9R,11E)-5-(3-2-(methoxycarbonyl)phenyl)prop-2-en-1-ylideneamino)-11-ethylidene-5,6,9,10-tetrahydro-7-methyl-5,9-methanocycloocta[b]pyridin-2(1H)-one:

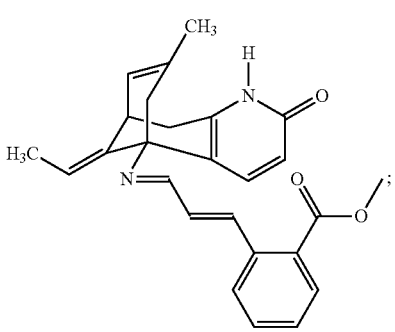

36) (5R,9R,11E)-5-(3-3-(methoxycarbonyl)phenyl)prop-2-en-1-ylideneamino)-11-ethylidene-5,6,9,10-tetrahydro-7-methyl-5,9-methanocycloocta[b]pyridin-2(1H)-one:

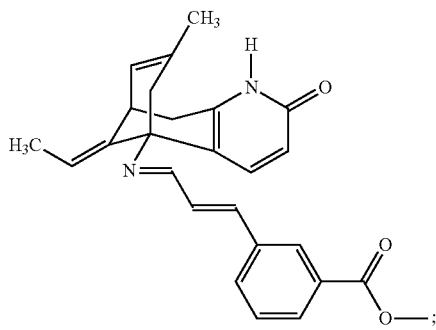

37) (5R,9R,11E)-5-(3-4-(methoxycarbonyl)phenyl)prop-2-en-1-ylideneamino)-11-ethylidene-5,6,9,10-tetrahydro-7-methyl-5,9-methanocycloocta[b]pyridin-2(1H)-one:

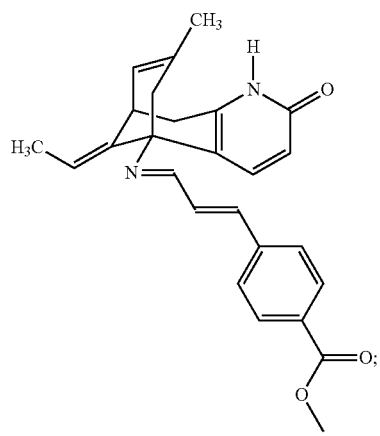

38) (5R,9R,11E)-5-(3-2-(ethoxycarbonyl)phenyl)prop-2-en-1-ylideneamino)-11-ethylidene-5,6,9,10-tetrahydro-7-methyl-5,9-methanocycloocta[b]pyridin-2(1H)-one:

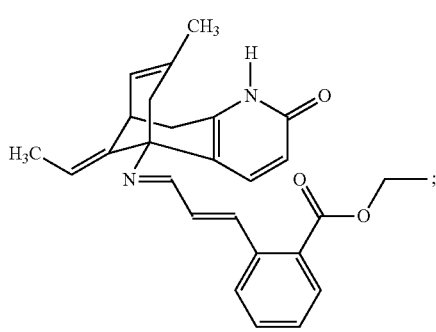

39) (5R,9R,11E)-5-(3-3-(ethoxycarbonyl)phenyl)prop-2-en-1-ylideneamino)-11-ethylidene-5,6,9,10-tetrahydro-7-methyl-5,9-methanocycloocta[b]pyridin-2(1H)-one:

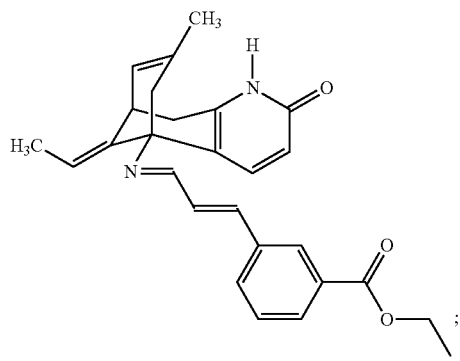

40) (5R,9R,11E)-5-(3-4-(ethoxycarbonyl)phenyl)prop-2-en-1-ylideneamino)-11-ethylidene-5,6,9,10-tetrahydro-7-methyl-5,9-methanocycloocta[b]pyridin-2(1H)-one:

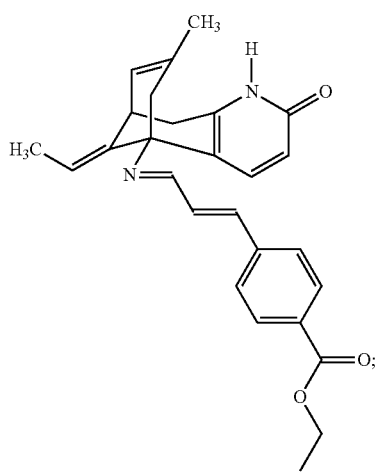

41) (5R,9R,11E)-5-(3-2-(methylaminocarbonyl)phenyl)prop-2-en-1-ylideneamino)-11-ethylidene-5,6,9,10-tetrahydro-7-methyl-5,9-methanocycloocta[b]pyridin-2(1H)-one:

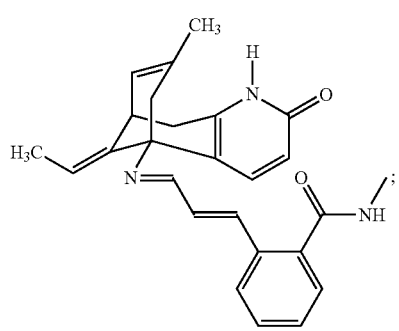

42) (5R,9R,11E)-5-(3-3-(methylaminocarbonyl)phenyl)prop-2-en-1-ylideneamino)-11-ethylidene-5,6,9,10-tetrahydro-7-methyl-5,9-methanocycloocta[b]pyridin-2(1H)-one:

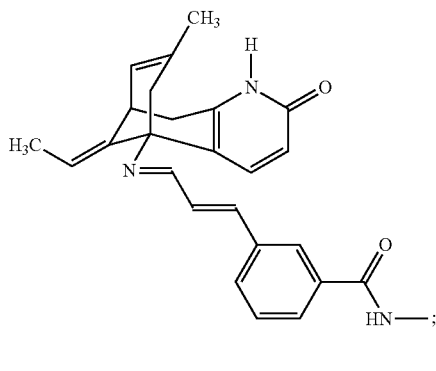

43) (5R,9R,11E)-5-(3-4-(methylaminocarbonyl)phenyl) prop-2-en-1-ylideneamino)-11-ethylidene-5,6,9,10-tetrahydro-7-methyl-5,9-methanocycloocta[b]pyridin-2(1H)-one:

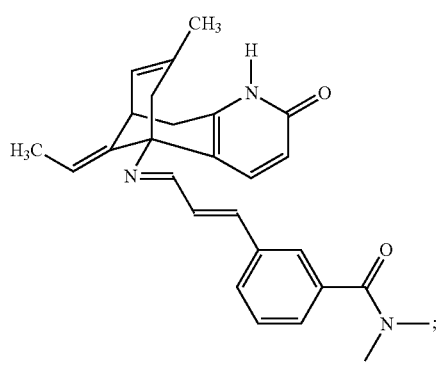

46) (5R,9R,11E)-5-(3-4-(dimethylaminocarbonyl)phenyl) prop-2-en-1-ylideneamino)-11-ethylidene-5,6,9,10-tetrahydro-7-methyl-5,9-methanocycloocta[b]pyridin-2(1H)-one:

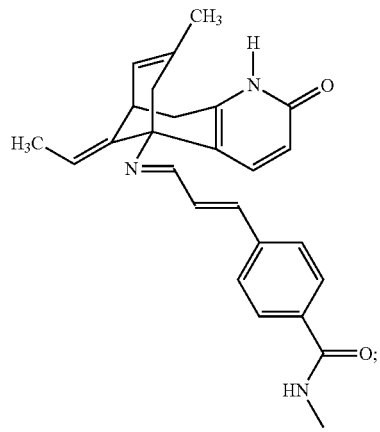

44) (5R,9R,11E)-5-(3-2-(dimethylaminocarbonyl)phenyl) prop-2-en-1-ylideneamino)-11-ethylidene-5,6,9,10-tetrahydro-7-methyl-5,9-methanocycloocta[b]pyridin-2(1H)-one:

47) (5R,9R,11E)-5-(3-2-(propoxycarbonyl)phenyl)prop-2-en-1-ylideneamino)-11-ethylidene-5,6,9,10-tetrahydro-7-methyl-5,9-methanocycloocta[b]pyridin-2(1H)-one:

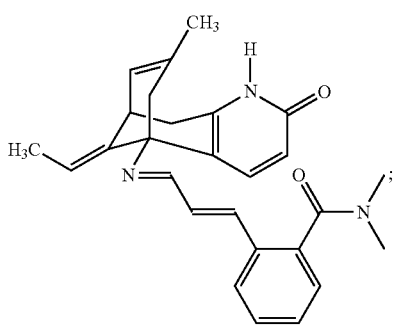

45) (5R,9R,11E)-5-(3-3-(dimethylaminocarbonyl)phenyl) prop-2-en-1-ylideneamino)-11-ethylidene-5,6,9,10-tetrahydro-7-methyl-5,9-methanocycloocta[b]pyridin-2(1H)-one:

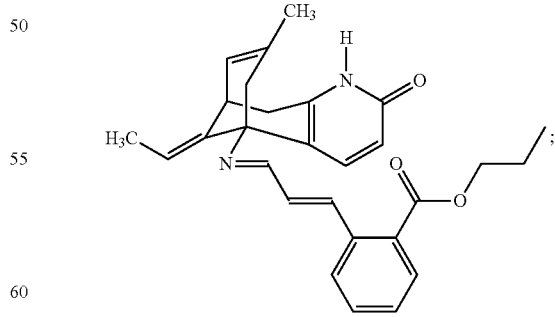

48) (5R,9R,11E)-5-(3-3-(propoxycarbonyl)phenyl)prop-2-en-1-ylideneamino)-11-ethylidene-5,6,9,10-tetrahydro-7-methyl-5,9-methanocycloocta[b]pyridin-2(1H)-one:

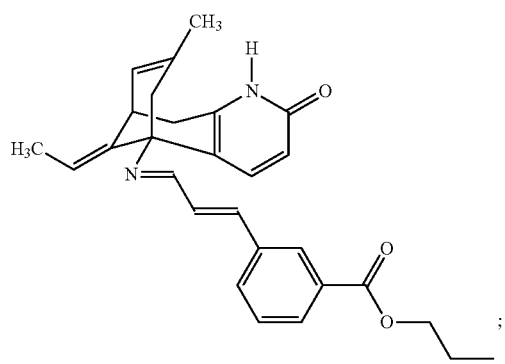

49) (5R,9R,11E)-5-(3-4-(propoxycarbonyl)phenyl)prop-2-en-1-ylideneamino)-11-ethylidene-5,6,9,10-tetrahydro-7-methyl-5,9-methanocycloocta[b]pyridin-2(1H)-one:

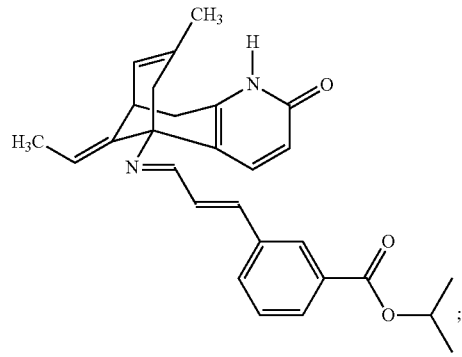

52) (5R,9R,11E)-5-(3-4-(isopropoxycarbonyl)phenyl)prop-2-en-1-ylideneamino)-11-ethylidene-5,6,9,10-tetrahydro-7-methyl-5,9-methanocycloocta[b]pyridin-2(1H)-one:

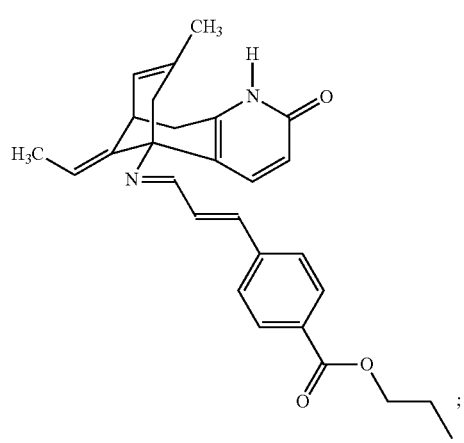

50) (5R,9R,11E)-5-(3-2-(isopropoxycarbonyl)phenyl)prop-2-en-1-ylideneamino)-11-ethylidene-5,6,9,10-tetrahydro-7-methyl-5,9-methanocycloocta[b]pyridin-2(1H)-one:

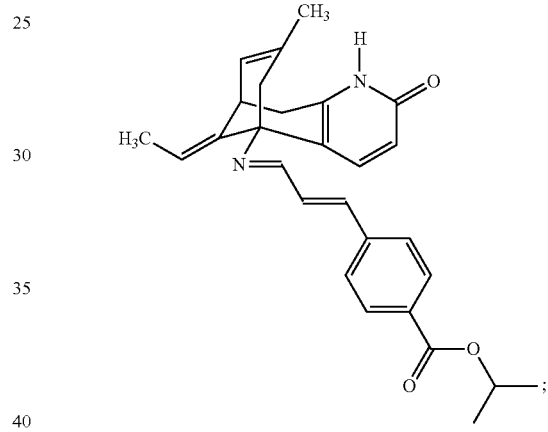

53) (5R,9R,11E)-5-(3-2-(ethylaminocarbonyl)phenyl)prop-2-en-1-ylideneamino)-11-ethylidene-5,6,9,10-tetrahydro-7-methyl-5,9-methanocycloocta[b]pyridin-2(1H)-one:

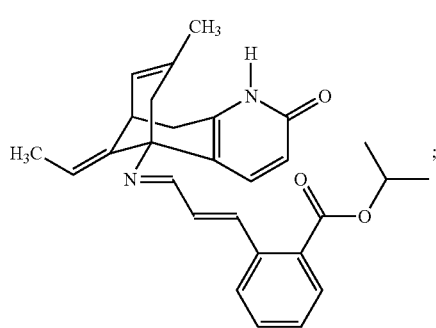

51) (5R,9R,11E)-5-(3-3-(isopropoxycarbonyl)phenyl)prop-2-en-1-ylideneamino)-11-ethylidene-5,6,9,10-tetrahydro-7-methyl-5,9-methanocycloocta[b]pyridin-2(1H)-one:

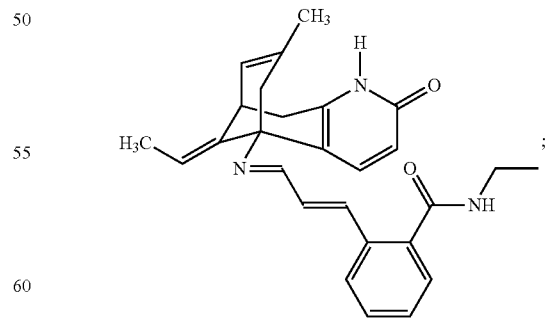

54) (5R,9R,11E)-5-(3-3-(ethylaminocarbonyl)phenyl)prop-2-en-1-ylideneamino)-11-ethylidene-5,6,9,10-tetrahydro-7-methyl-5,9-methanocycloocta[b]pyridin-2(1H)-one:

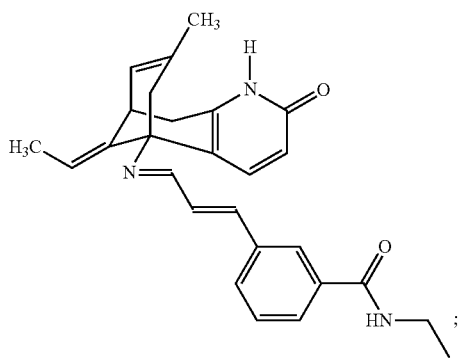

55) (5R,9R,11E)-5-(3-4-(ethylaminocarbonyl)phenyl)prop-2-en-1-ylideneamino)-11-ethylidene-5,6,9,10-tetrahydro-7-methyl-5,9-methanocycloocta[b]pyridin-2(1H)-one:

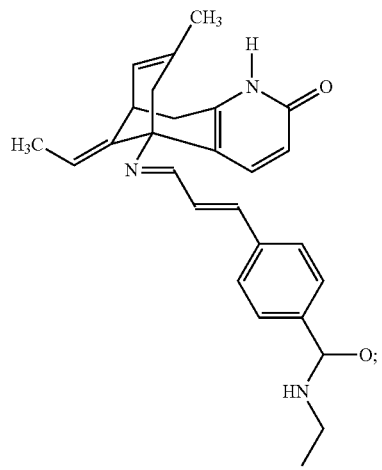

56) (5R,9R,11E)-5-(3-(2-fluorophenyl)prop-2-en-1-ylideneamino)-11-ethylidene-5,6,9,10-tetrahydro-7-methyl-5,9-methanocycloocta[b]pyridin-2(1H)-one:

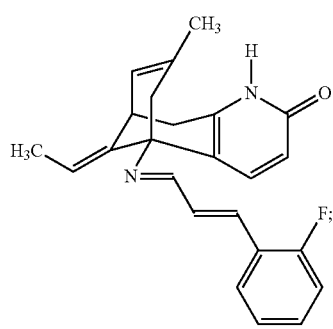

57) (5R,9R,11E)-5-(3-(3-fluorophenyl)prop-2-en-1-ylideneamino)-11-ethylidene-5,6,9,10-tetrahydro-7-methyl-5,9-methanocycloocta[b]pyridin-2(1H)-one:

58) (5R,9R,11E)-5-(3-(4-fluorophenyl)prop-2-en-1-ylideneamino)-11-ethylidene-5,6,9,10-tetrahydro-7-methyl-5,9-methanocycloocta[b]pyridin-2(1H)-one:

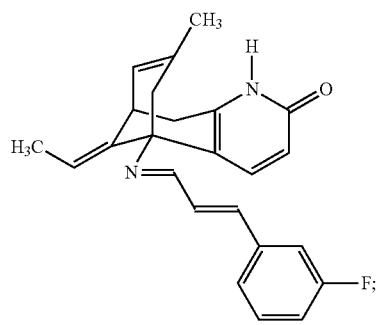

59) (5R,9R,11E)-5-(3-(2-acetylaminophenyl)prop-2-en-1-ylideneamino)-11-ethylidene-5,6,9,10-tetrahydro-7-methyl-5,9-methanocycloocta[b]pyridin-2(1H)-one:

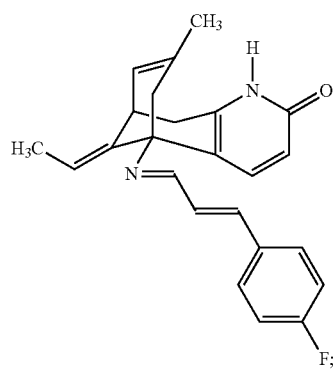

60) (5R,9R,11E)-5-(3-(3-acetylaminophenyl)prop-2-en-1-ylideneamino)-11-ethylidene-5,6,9,10-tetrahydro-7-methyl-5,9-methanocycloocta[b]pyridin-2(1H)-one:

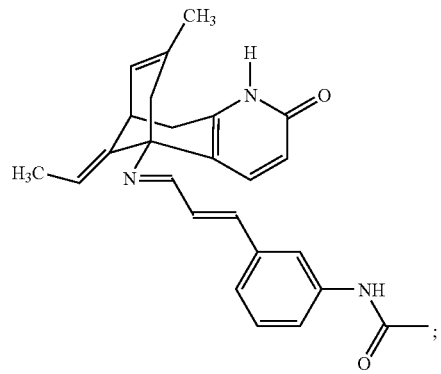

61) (5R,9R,11E)-5-(3-(4-acetylaminophenyl)prop-2-en-1-ylideneamino)-11-ethylidene-5,6,9,10-tetrahydro-7-methyl-5,9-methanocycloocta[b]pyridin-2(1H)-one:

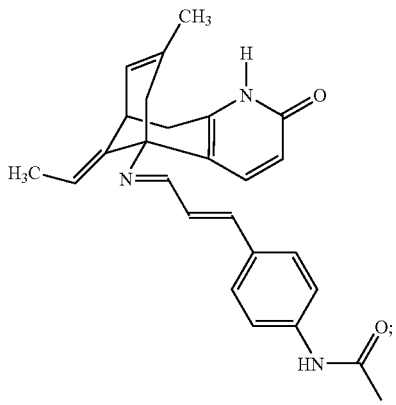

62) (5R,9R,11E)-5-(3-(2-diethylaminophenyl)prop-2-en-1-ylideneamino)-11-ethylidene-5,6,9,10-tetrahydro-7-methyl-5,9-methanocycloocta[b]pyridin-2(1H)-one:

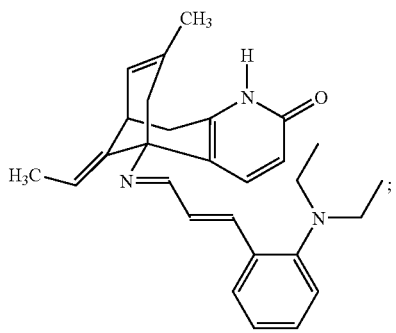

63) (5R,9R,11E)-5-(3-(3-diethylaminophenyl)prop-2-en-1-ylideneamino)-11-ethylidene-5,6,9,10-tetrahydro-7-methyl-5,9-methanocycloocta[b]pyridin-2(1H)-one:

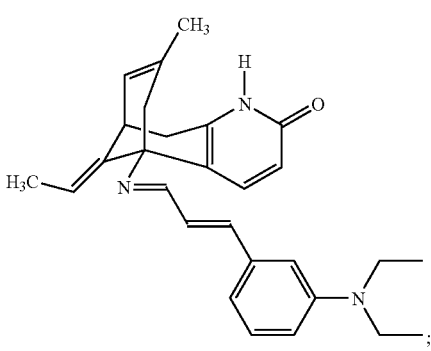

64) (5R,9R,11E)-5-(3-(4-diethylaminophenyl)prop-2-en-1-ylideneamino)-11-ethylidene-5,6,9,10-tetrahydro-7-methyl-5,9-methanocycloocta[b]pyridin-2(1H)-one:

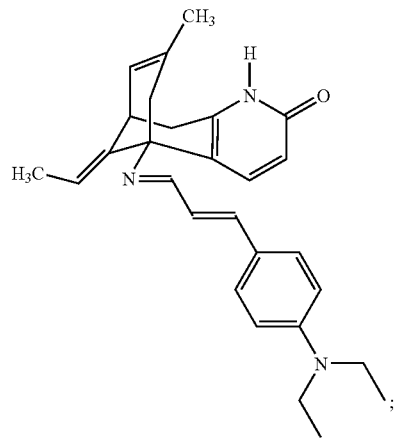

65) (5R,9R,11E)-5-(3-(2-nitrophenyl)prop-2-en-1-ylideneamino)-11-ethylidene-5,6,9,10-tetrahydro-7-methyl-5,9-methanocycloocta[b]pyridin-2(1H)-one:

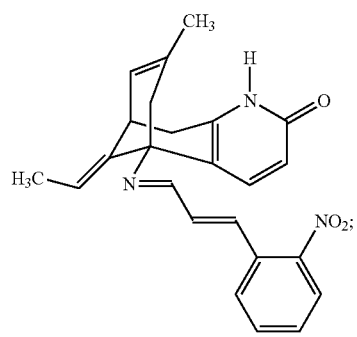

66) (5R,9R,11E)-5-(3-(anthracen-9-yl)prop-2-en-1-ylideneamino)-11-ethylidene-5,6,9,10-tetrahydro-7-methyl-5,9-methanocycloocta[b]pyridin-2(1H)-one:

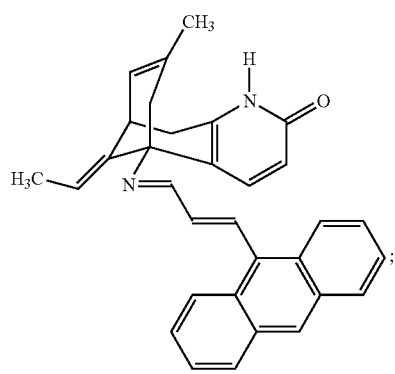

67) (5R,9R,11E)-5-(3-methyl-3-phenylprop-2-en-1-ylideneamino)-11-ethylidene-5,6,9,10-tetrahydro-7-methyl-5,9-methanocycloocta[b]pyridin-2(1H)-one:

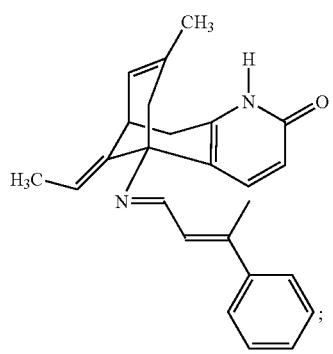

68) (5R,9R,11E)-5-(2-methyl-3-phenylprop-2-en-1-ylideneamino)-11-ethylidene-5,6,9,10-tetrahydro-7-methyl-5,9-methanocycloocta[b]pyridin-2(1H)-one:

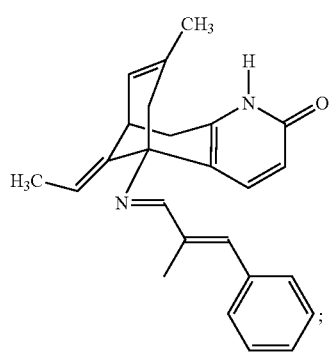

69) (5R,9R,11E)-5-(2-chloro-3-phenylprop-2-en-1-ylideneamino)-11-ethylidene-5,6,9,10-tetrahydro-7-methyl-5,9-methanocycloocta[b]pyridin-2(1H)-one:

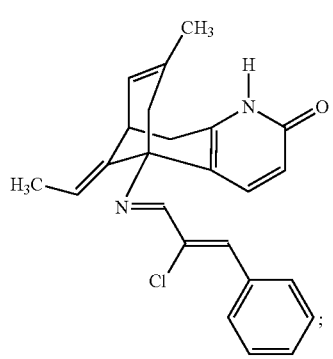

70) (5R,9R,11E)-5-(3-chloro-3-phenylprop-2-en-1-ylideneamino)-11-ethylidene-5,6,9,10-tetrahydro-7-methyl-5,9-methanocycloocta[b]pyridin-2(1H)-one:

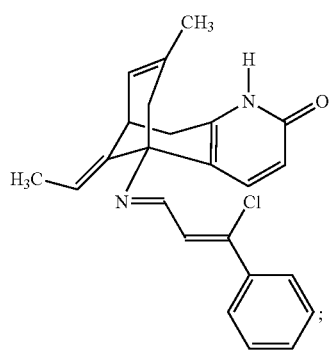

71) (5R,9R,11E)-5-(5-phenylpent-2,4-dien-1-ylideneamino)-11-ethylidene-5,6,9,10-tetrahydro-7-methyl-5,9-methanocycloocta[b]pyridin-2(1H)-one:

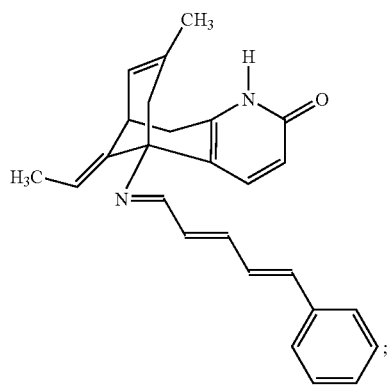

72) (5R,9R,11E)-5-(7-phenylhept-2,4,6-trien-1-ylideneamino)-11-ethylidene-5,6,9,10-tetrahydro-7-methyl-5,9-methanocycloocta[b]pyridin-2(1H)-one:

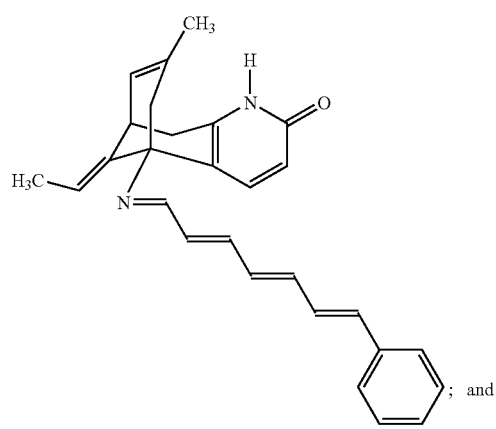

; and 73) (5R,9R,11E)-5-(2-(indan-1-ylidene)-ethylideneamino)-11-ethylidene-5,6,9,10-tetrahydro-7-methyl-5,9-methanocycloocta[b]pyridin-2(1H)-one:

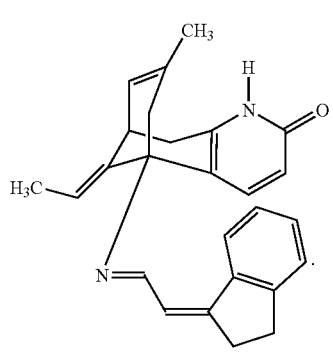

The compounds of Formula I release huperzine A after p.o. administration. The amount of huperzine A released in artificial gastric fluid at various time intervals after administration of (5R,9R,11E)-5-(3-phenylprop-2-en-1-ylideneamino)-11-ethylidene-5,6,9,10-tetrahydro-7-methyl-5,9-methanocycloocta[b]pyridin-2(1H)-one is listed in Table 2. Data in Table 2 shows that (5R,9R,11E)-5-(3-phenylprop-2-en-1-ylideneamino)-1-ethylidene-5,6,9,10-tetrahydro-7-methyl-5,9-methanocycloocta[b]pyridin-2(H)-one can completely release an equivalent amount of huperzine A in 3 hours. Accordingly, (5R,9R,11E)-5-(3-phenylprop-2-en-1-ylideneamino)-11-ethylidene-5,6,9,10-tetrahydro-7-methyl-5,9-methanocycloocta[b]pyridin-2(1H)-one is a pro-drug of huperzine A, and releases huperzine A in a sustained fashion. Sustained release of huperzine A can well explain lower toxicity of compounds of Formula I compared with Huperzine A (see Table 1). Furthermore, it reveals the reason that the analgesic effect of the compounds of Formula I has a longer duration than that of Huperzine A.

TABLE 1

Acute toxicity ($LD_{50}$) in mice

| Compound of | Type of administration | $LD_{50}$ (mg/kg) |
|---|---|---|
| Example 1 | oral | 3.8 |
| Example 2 | oral | 26.5 |
| Example 3 | oral | 29.8 |
| Example 14 | oral | 35.6 |
| Example 23 | oral | 43.2 |

In summary, compounds of Formula I comprise a series of low toxicity analgesic drugs with significant, enduring analgesic effects.

In other aspect, this invention relates to a method of preparation of the compounds of Formula I,

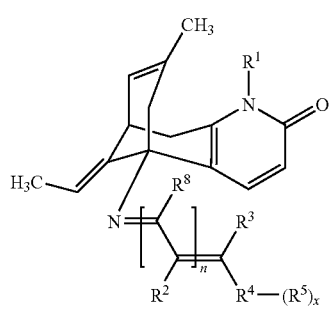

a pharmaceutically-acceptable salt, or a hydrate thereof, which is useful in the treatment of pain, functional pain syndrome, or organogenic pain syndrome; wherein $R^1$ is H, or $C_{1-4}$ alkyl; $R^2$ is H, halogen, or $C_{1-4}$ alkyl; $R^3$ is H, halogen, or $C_{1-4}$ alkyl, and $R^4$ is $C_{1-6}$ alkyl, aryl; or $=CR^3R^4$ is cyclopentylidene, cyclohexylidene, 1-methylpiperidin-4-ylidene, or inden-1-ylidene; $R^5$ is independently at each occurrence F, Cl, Br, $CF_3$, $R^9$, $OR^9$, $NR^9R^{10}$, $NO_2$, CN, $COOR^9$, $O_2CR^9$, $CONR^9R^{10}$, $NR^9C(O)R^{10}$, heterocyclic group, aryl, or a group of Formula II

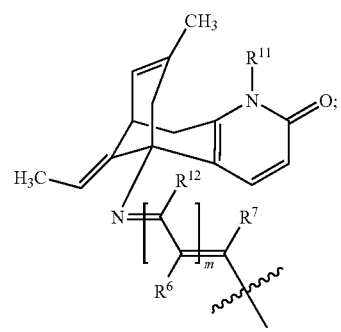

$R^6$ is H, halogen, or $C_{1-4}$ alkyl; $R^7$ is H, halogen, or $C_{1-4}$ alkyl; $R^8$ is H, $C_1$, alkyl group; $R^9$ is H, or $C_{1-6}$ alkyl; $R^{10}$ is H, or $C_{1-6}$ alkyl; $R^{11}$ is H, or $C_{1-4}$ alkyl; $R^{12}$ is H, or $C_{1-4}$ alkyl; m is 0, 1, or 2; when $R^5$ is F, Cl, Br, $CF_3$, $R^9$, $OR^9$, $NR^9R^{10}$, $NO_2$, CN, $COOR^9$, $O_2CR^9$, $CONR^9R^{10}$, $NR^9C(O)R^{10}$, heterocyclic group, or aryl, n is 1, 2, 3, or 4; when $R^5$ is the group of Formula II, n is 0, 1, 2, 3, or 4; x is 0, 1, 2, 3, or 4.

The method of preparation of compounds of Formula I comprises the following steps: (a) (i) contacting a compound of Formula III with malonic acid to yield a compound of Formula V; or (ii) contacting a compound of Formula III with trimethyl phosphonoacetate to give a compound of Formula IV and hydrolyzing the compound of Formula IV to yield a compound of Formula V; (b) contacting the compound of Formula V with carbonyldiimidazole to yield a corresponding acylated imidazole, and reducing the corresponding acylated imidazole to yield a compound of Formula VI; (c) oxidizing the compound of Formula VI to yield a compound of Formula VII; and (d) contacting the compound of Formula VII with a compound of Formula VIII to yield the compound of Formula I, wherein

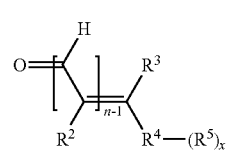

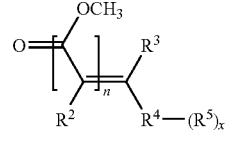

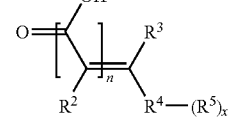

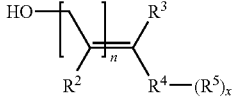

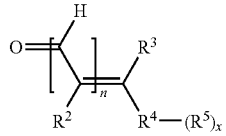

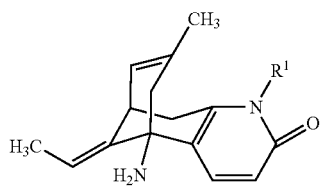

VIII $R^1$ is H, or $C_{1-4}$ alkyl; $R^2$ is H, halogen, or $C_{1-4}$ alkyl; $R^3$ is H, halogen, or $C_{1-4}$ alkyl, and $R^4$ is $C_{1-6}$ alkyl, aryl; or $=CR^3R^4$ is cyclopentylidene, cyclohexylidene, 1-methylpiperidin-4-ylidene, or inden-1-ylidene; $R^5$ is independently at each occurrence F, Cl, Br, $CF_3$, $R^9$, $OR^9$, $NR^9R^{10}$, $NO_2$, CN, $COOR^9$, $O_2CR^9$, $CONR^9R^{10}$, $NR^9C(O)R^{10}$, heterocyclic group, aryl, or a group of Formula II

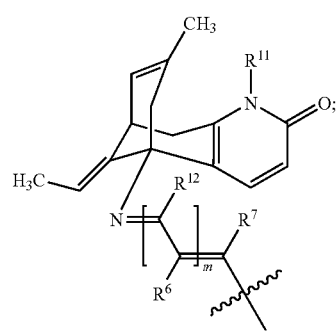

II $R^6$ is H, halogen, or $C_{1-4}$ alkyl; $R^7$ is H, halogen, or $C_{1-4}$ alkyl; $R^8$ is H, $C_{1-4}$ alkyl group; $R^9$ is H, or $C_{1-6}$ alkyl; $R^{10}$ is H, or $C_{1-6}$ alkyl; $R^{11}$ is H, or $C_{1-4}$ alkyl; $R^{12}$ is H, or $C_{1-4}$ alkyl; m is 0, 1, or 2; when $R^5$ is F, Cl, Br, $CF_3$, $R^9$, $OR^9$, $NR^9R^{10}$, $NO_2$, CN, $COOR^9$, $O_2CR^9$, $CONR^9R^{10}$, $NR^9C(O)R^{10}$, heterocyclic group, or aryl, n is 1, 2, 3, or 4; when $R^5$ is the group of Formula II, n is 0, 1, 2, 3, or 4; x is 0, 1, 2, 3, or 4.

A pharmaceutical preparation of the invention comprises in addition to at least one compound of Formula I, one or more carrier materials, bulking agents, solvents, diluents, colorants, and/or adhesives. The choice of type and amount of these adjuvants depends on the mode of administration including gastrointestinal, oral, buccal, intravenous, abdominal, dermal, intramuscular, nasal, ocular, pulmonary, anal, vaginal, percutaneous, hypodermic, or transdermal.

Pharmaceutical preparations according to this invention can be sustained-release.

Compounds of this invention can be mixed with other active ingredients and used as a complex preparations.

Pain treated by methods of this invention comprises painful discomforts, functional pain syndrome, organogenic pain syndrome, or tissue pain syndrome, including but not limiting to: neuropathic headache, migraine, primary fibromyalgia, postoperative pain, visceral pain, toothache, neuralgia, courbature, arthralgia, menstrual pain, or pain resulting from amputation, tumoral denervation, traumatic denervation, nerve injury, inflammation, or autoimmune disorder.

BRIEF DESCRIPTION OF THE DRAWINGS

The invention is described herein below with reference to accompanying drawings, in which the sole FIGURE shows time curve representing the amount of Huperzine A released by H064-5-2 in artificial gastric fluid.

DETAILED DESCRIPTION OF THE INVENTION

EXAMPLES

Intermediate 1

3-(3-Methylphenyl)prop-2-en-1-acid 1.2 g 3-methylbenzaldehyde and 1.04 g malonic acid were combined in 5 mL pyridine, and heated in an oil bath for 7 hours, then cooled. 40 mL water and 5 mL saturated aqueous $Na_2CO_3$ solution were added to the crude reaction mixture, which was then extracted twice with ethyl acetate. The pH of the aqueous phase was adjusted with 6N hydrochloric acid until no more solid precipitated, filtrated, and the filter cake was washed with 1.5N hydrochloric acid, and dried. 330 mg white solid was obtained.

Intermediate 2

3-(3-Methylphenyl)prop-2-en-1-ol

Intermediate 1 was dissolved in 20 mL anhydrous THF, 500 mg CDI was added with stirring at ambient temperature, and stirred for 24 hours at room temperature. This reaction mixture was labeled as A. 539 mg $NaBH_4$ was dissolved in 40 mL THF/water (1:1), and the solution was labeled as B. Solution A was added to solution B dropwise, stirred for 40 min, and the pH of this mixture was adjusted to 3 with 6N hydrochloric acid. The mixture was extracted with ethyl acetate twice, and the ethyl acetate layers were combined and washed with 1.5N hydrochloric acid twice, saturated $Na_2CO_3$ three times, water once, saturated aqueous NaCl solution once, dried with anhydrous $MgSO_4$ for 2 hours, filtered, and the filtrate was dried under vacuum, yielding 210 mg of title product.

Intermediate 3

3-(3-Methylphenyl)prop-2-enal

Intermediate 2 was dissolved in 20 mL acetone, 1.111 g $MnO_2$ was added, stirred at ambient temperature for three days, filtrated, and the filtrate was dried under vacuum to give 230 mg of crude title product.

The synthetic process employed for the preparation of intermediates 1-3 was employed to yield the following compounds:

| | Compound |
|---|---|
| Intermediate 4 | 3-(3-Chlorophenyl)prop-2-en-1-al |
| Intermediate 5 | 3-(2-Chlorophenyl)prop-2-en-1-al |
| Intermediate 6 | 3-(4-Chlorophenyl)prop-2-en-1-al |
| Intermediate 7 | 3-(2-Methylphenyl)prop-2-en-1-al |
| Intermediate 8 | 3-(4-Methylphenyl)prop-2-en-1-al |
| Intermediate 9 | 3-(3-Methoxyphenyl)prop-2-en-1-al |
| Intermediate 10 | 3-(4-Methoxyphenyl)prop-2-en-1-al |
| Intermediate 11 | 3-(2-Methoxyphenyl)prop-2-en-1-al |
| Intermediate 12 | 3-(3-Bromophenyl)prop-2-en-1-al |
| Intermediate 13 | 3-(2-Bromophenyl)prop-2-en-1-al |
| Intermediate 14 | 3-(4-Bromophenyl)prop-2-en-1-al |
| Intermediate 15 | 3-(Pyridin-4-yl)prop-2-en-1-al |
| Intermediate 16 | 5-Phenylpenta-2,4-dien-1-al |
| Intermediate 17 | 3-(Naphthalen-1-yl)prop-2-en-1-al |
| Intermediate 18 | 3-(Naphthalen-2-yl)prop-2-en-1-al |
| Intermediate 19 | 3-(Furan-1-yl)prop-2-en-1-al |
| Intermediate 20 | 3-(4-(2-Formylethenyl)phenyl)prop-2-en-1-al |
| Intermediate 21 | 3-(Anthracen-9-yl)prop-2-en-1-al |
| Intermediate 22 | 2-Methyl-3-phenylprop-2-en-1-al |

Intermediate 23

Methyl 2-cyclohexylideneacetate 2.184 g trimethylphosphonoacetate was dissolved in DCM, stirred on ice-water bath, and 384 mg NaH was added. After 6 hours 980 mg cyclohexanone was added into the reaction flask, and stirred at ambient temperature overnight. The next day, the reaction mixture was washed with water twice, saturated aqueous NaCl solution once, dried over anhydrous MgSO$_4$ for 2 hours, filtrated, and the filtrate was dried under vacuum to give 1.227 g of the title crude product.

Intermediate 24

2-Cyclohexylideneacetic acid

Crude intermediate 23 was dissolved in 15 mL THF and 15 mL methanol. 30 mL aqueous 1N LiOH solution was added, and it was stirred at ambient temperature overnight. The next day, pH of the reaction system was adjusted to 1 with 6N hydrochloric acid, and the reaction mixture was extracted with ethyl acetate three times, and the ethyl acetate layers were combined and washed with water once, saturated aqueous NaCl solution once, dried over anhydrous MgSO$_4$ for 2 hours, filtrated, and the filtrate was dried under vacuum to give 0.796 g of oily crude title product.

Intermediate 25

2-Cyclohexylideneacetaldehyde

The synthetic process employed for the preparation of intermediates 2-3 was employed to yield 2-cyclohexylideneacetaldehyde starting from intermediate 24.

Intermediate 26

3-Methyl-3-phenylprop-2-enal

The synthetic process employed for the preparation of intermediates 23-25 was employed to yield 3-methyl-3-phenylprop-2-enal.

Intermediate 27

2-Bromo-3-phenylprop-2-enal 1.33 g (10 mmol) cinnamaldehyde was dissolved in 5 mL glacial acetic acid and cooled on an ice-water bath. 1.62 g bromine was added, and anhydrous K$_2$CO$_3$ was then added, and it was stirred until no gas was evolving. After refluxing for 30 min, the reaction mixture was poured into 100 mL cold water with stirring, extracted with 50 mL ethyl ether three times. The combined ethyl ether layers were washed with water one time, saturated aqueous NaCl solution one time, dried over MgSO$_4$ for 2 hours, filtrated, and the filtrate was dried under vacuum, and washed with anhydrous ethyl ether: petroleum ether (1:1) to give the title compound as light yellow powder.

Example 1

(5R,9R,11E)-5-amino-11-ethylidene-5,6,9,10-tetrahydro-7-methyl-5,9-methanocycloocta[b]pyridin-2 (1H)-one ((−)-huperzine A)

The title compound was purchased from Shanghai Tauto Biotech Co., Ltd.

Example 2

(5R,9R,11E)-5-(3-phenylprop-2-en-1-ylideneamino)-11-ethylidene-5,6,9,10-tetrahydro-7-methyl-5,9-methanocycloocta[b]pyridin-2(1H)-one 20 mg Huperzine A, and 77 mg cinnamaldehyde were refluxed in 2 mL isopropanol for 3 hours. Solvent was removed under vacuum. The crude reaction mixture was dissolved in 3 mL anhydrous THF and purified with prep. TLC (CHCl$_3$: methanol=9:1) to give 28 mg of title product. MS: 357 (M+H).

Example 3

(5R,9R,11E)-5-(2-methyl-3-phenylprop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 2-methyl-3-phenylprop-2-en-1-al instead of cinnamaldehyde. MS: 371 (M+H).

Example 4

(5R,9R,11E)-5-(3-(3-methylphenyl)prop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 3-(3-methylphenyl)prop-2-en-1-al instead of cinnamaldehyde. MS: 371 (M+H).

Example 5

(5R,9R,11E)-5-(3-(2-methylphenyl)prop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 3-(2-methylphenyl)prop-2-en-1-al instead of cinnamaldehyde. MS: 371 (M+H).

Example 6

(5R,9R,11E)-5-(3-(4-methylphenyl)prop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 3-(4-methylphenyl)prop-2-en-1-al instead of cinnamaldehyde. MS: 371 (M+H).

Example 7

(5R,9R,11E)-5-(3-methyl-3-phenylprop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 3-methyl-3-phenylprop-2-en-1-al instead of cinnamaldehyde. MS: 371 (M+H).

Example 8

(5R,9R,11E)-5-(5-phenylpenta-2,4-dien-1-ylidene-amino)-11-ethylidene-5,6,9,10-tetrahydro-7-methyl-5,9-methanocycloocta[b]pyridin-2(1H)-one By the method of Example 2, the title compound was prepared from 5-phenylpenta-2,4-dien-1-al instead of cinnamaldehyde. MS: 383 (M+H).

Example 9

(5R,9R,11E)-5-(7-phenylhepta-2,4,6-trien-1-ylidene-amino)-11-ethylidene-5,6,9,10-tetrahydro-7-methyl-5,9-methanocycloocta[b]pyridin-2(1H)-one By the method of Example 2, the title compound was prepared from 7-phenylhepta-2,4,6-trien-1-al instead of cinnamaldehyde. MS: 409 (M+H).

Example 10

(5R,9R,11E)-5-(2-bromo-3-phenylprop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 2-bromo-3-phenylprop-2-en-1-al instead of cinnamaldehyde. MS: 435 (M+H).

Example 11

(5R,9R,11E)-5-(3-(3-bromophenyl)prop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 3-(3-bromophenyl)prop-2-en-1-al instead of cinnamaldehyde. MS: 435 (M+H).

Example 12

(5R,9R,11E)-5-(3-(2-bromophenyl)prop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 3-(2-bromophenyl)prop-2-en-1-al instead of cinnamaldehyde. MS: 435 (M+H).

Example 13

(5R,9R,11E)-5-(3-(4-bromophenyl)prop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 3-(4-bromophenyl)prop-2-en-1-al instead of cinnamaldehyde. MS: 435 (M+H).

Example 14

(5R,9R,11E)-5-(3-(4-chlorophenyl)prop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 3-(4-chlorophenyl)prop-2-en-1-al instead of cinnamaldehyde. MS: 391 (M+H).

Example 15

(5R,9R,11E)-5-(3-(3-chlorophenyl)prop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 3-(3-chlorophenyl)prop-2-en-1-al instead of cinnamaldehyde. MS: 391 (M+H).

Example 16

(5R,9R,11E)-5-(3-(2-chlorophenyl)prop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 3-(2-chlorophenyl)prop-2-en-1-al instead of cinnamaldehyde. MS: 391 (M+H).

Example 17

(5R,9R,11E)-5-(3-(4-methoxylphenyl)prop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 3-(4-methoxylphenyl)prop-2-en-1-al instead of cinnamaldehyde. MS: 387 (M+H).

Example 18

(5R,9R,11E)-5-(3-(2-methoxylphenyl)prop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 3-(2-methoxylphenyl)prop-2-en-1-al instead of cinnamaldehyde. MS: 387 (M+H).

Example 19

(5R,9R,11E)-5-(3-(3-methoxylphenyl)prop-2-en-1-ylideneamino)-11-ethylidene-5,6,9,10-tetrahydro-7-methyl-5,9-methanocycloocta[b]pyridin-2(1H)-one By the method of Example 2, the title compound was prepared from 3-(3-methoxylphenyl)prop-2-en-1-al instead of cinnamaldehyde. MS: 387 (M+H).

Example 20

(5R,9R,11E)-5-(3-(pyridin-4-yl)prop-2-en-1-ylidene-amino)-11-ethylidene-5,6,9,10-tetrahydro-7-methyl-5,9-methanocycloocta[b]pyridin-2(1H)-one By the method of Example 2, the title compound was prepared from 3-(pyridin-4-yl)prop-2-en-1-al instead of cinnamaldehyde. MS: 358 (M+H).

Example 21

(5R,9R,11E)-5-(3-(furan-2-yl)prop-2-en-1-ylidene-amino)-11-ethylidene-5,6,9,10-tetrahydro-7-methyl-5,9-methanocycloocta[b]pyridin-2(1H)-one By the method of Example 2, the title compound was prepared from 3-(furan-2-yl)prop-2-en-1-al instead of cinnamaldehyde. MS: 347 (M+H).

Example 22

(5R,9R,11E)-5-(3-(naphthalen-2-yl)prop-2-en-1-ylideneamino)-11-ethylidene-5,6,9,10-1,7-dimethyl-5,9-methanocycloocta[b]pyridin-2(1H)-one By the method of Example 2, the title compound was prepared from 3-(naphthalen-2-yl)prop-2-en-1-al instead of cinnamaldehyde. MS: 407 (M+H).

Example 23

(5R,9R,11E)-5-(3-(naphthalen-1-yl)prop-2-en-1-ylideneamino)-11-ethylidene-5,6,9,10-1,7-dimethyl-5,9-methanocycloocta[b]pyridin-2(1H)-one By the method of Example 2, the title compound was prepared from 3-(naphthalen-1-yl)prop-2-en-1-al instead of cinnamaldehyde. MS: 407 (M+H).

Example 24

(5R,9R,11E)-5-(2-(cyclohexylidene)ethylidene-amino)-11-ethylidene-5,6,9,10-tetrahydro-1,7-dimethyl-5,9-methanocycloocta[b]pyridin-2(1H)-one By the method of Example 2, the title compound was prepared from 2-(cyclohexylidene)acetaldehyde instead of cinnamaldehyde. MS: 381(M+$CH_3OH$+H).

Example 25

(5R,9R,11E)-5-(3-(4-dimethylaminophenyl)prop-2-en-1-ylideneamino)-11-ethylidene-5,6,9,10-1,7-dimethyl-5,9-methanocycloocta[b]pyridin-2(1H)-one By the method of Example 2, the title compound was prepared from 3-(4-dimethylaminophenyl)prop-2-en-1-al instead of cinnamaldehyde. MS: 400 (M+H).

Example 26

(5R,9R,11E)-5-(3-(anthracen-9-yl)prop-2-en-1-ylideneamino)-11-ethylidene-5,6,9,10-1,7-dimethyl-5,9-methanocycloocta[b]pyridin-2(1H)-one By the method of Example 2, the title compound was prepared from 3-(anthracen-9-yl)prop-2-en-1-al instead of cinnamaldehyde. MS: 457 (M+H).

Example 27

By the method of Example 2, the title compound was prepared by the reaction of (E)-4-(2-formylvinyl)benzaldehyde instead of cinnamaldehyde with two equivalents of Huperzine A. MS: 609 (M+H).

Example 28

By the method of Example 2, the tile compound was prepared from the reaction of (E)-3-((E)-4-(2-formylvinyl)phenyl)-2-en-propanal instead of cinnamaldehyde with two equivalents of Huperzine A. MS: 635 (M+H).

Example 29

Studies of the release of Huperzine A by H064-5-2 (title compound of Example 2, (5R,9R,11E)-5-(3-phenylprop-2-en-1-ylideneamino)-11-ethylidene-5,6,9,10-tetrahydro-7-methyl-5,9-methanocycloocta[b]pyridin-2(1H)-one) in artificial gastric fluid Instruments and Reagents HPLC: Shimadzu SCL-10Avp, LC-10Atvp pump, SPD-M10Avp, DGU-14A. UV-VIS spectrophotometer: SHIMADZU UV-260. Huperzine A check sample (purity 99%). H064-5-2 (title compound of Example 2, (5R,9R,11E)-5-(3-phenylprop-2-en-1-ylideneamino)-11-ethylidene-5,6,9,10-tetrahydro-7-methyl-5,9-methanocycloocta[b]pyridin-2 (1H)-one): prepared by Tianjin Hemay BioTech Co. Ltd). Methanol (chromatographic grade). Purified $H_2O$. All other reagents are analytically pure.

Experiment and Results

1) Determination of wavelength: 1 mg cinnamaldehyde, 1 mg H064-5-2 and 1 mg Huperzine A check sample were precisely measured out. Methanol was then added to obtain a constant volume of 10 mL. 0.5 mL solution was subsequently taken out from the original solution to obtain a constant volume of 10 mL by adding methanol. Samples were scanned at 190-500 nm to identify absorption with methanol as blank. The results are the following: absorption peaks of H064-5-2 are 204.4 nm and 286.8 nm. The absorption peaks of cinnamaldehyde are 205.8 nm, 210.6 nm, 223.2 nm and 285.0 nm. The absorption peaks of huperzine A are 202.2 nm, 228.6 nm, 311.0 nm, 354.2 nm and 373.6 nm.

Conclusion: H064-5-2 has characteristic absorption peak at 287 nm.

2) Chromatography conditions: $C_{18}$ (150×4.6 mm, 5 μm), methanol/water (1:1) as mobile phase containing 0.02% triethanolamine. Flow rate 1 mL/min. Detection conditions are the following. detector: SPD-M10Avp. Detection wavelength: 287 nm. Injected sample volume: 20 μl.

3) Blank test: 0.3 mL grastric fluid was extracted, and 5 mL methanol was added to obtain a constant volume, injected sample volume is 20 μl, there are no peaks appearing at the retention times of the control sample.

4) Chromatogram of Huperzine A:

A) 1.0 mg Huperzine A check sample was precisely measured and added in a 10 mL volumetric flask; methanol was added to obtain a constant volume. 0.05 mL was then precisely extracted and 10 mL methanol was added to obtain a 10 mL constant volume, the injected sample volume is 20 μl. The chromatogram was recored.

B) 1.0 mg Huperzine A check sample was precisely measured and added in a 10 mL volumetric flask, gastric fluid was added to get a constant volume. 0.05 mL was taken out and methanol was added to get a constant volume of 10 mL with 0.5 ng/μl. The injected sample volume is 20 μl. Chromatogram was recorded.

5) Chromatogram of cinnamaldehyde: a small volume of cinnamaldehyde check sample was dissolved in methanol, and its chromatogram was recorded.

6) Standard curve: 1.0 mg Huperzine A check sample was precisely measured and added into a 10 mL volumetric flask, methanol was added to get a constant volume. 0.05 mL was taken out and methanol was added to it to get a constant volume of 10 mL, the concentration of which is 0.5 ng/μl. 2, 4, 5, 10, 25, and 50 μl solution were separately taken out, and injected according to the above stated chromatographic conditions. After linear regression analysis, the standard curve was plotted with the injected volume (ng) of huperzine A check sample as Y-axis, the area of main peak as x-axis. The results are shown in the Table 1.

TABLE 1

|  | 1 | 2 | 3 | 4 | 5 | 6 |
|---|---|---|---|---|---|---|
| V (ul) | 2 | 4 | 5 | 10 | 25 | 50 |
| W (ng) | 1 | 2 | 2.5 | 5 | 12.5 | 25 |
| A | 1088 | 2252 | 2856 | 5555 | 13859 | 28743 |

$y = 0.0008711 x + 0.1091$; $r = 0.9998$; linear range: 1-25 ng.

7) Sample measurement: 1.0 mg H064-5-2 sample was precisely measured, dissolved in gastric fluid with 2 min ultrasound; a constant volume of 10 mL with the concentration of 0.1 mg/mL was then obtained. 0.03 mL was precisely extracted at prescribed times, and methanol was added to get a constant volume of 5 mL, which was measured. The main peak area of Huperzine A was recorded, and the concentration was determined to be 0.6 ng/μl. The injected sample volume was 20 μl (12 ng). The results are listed in Table 2 and in FIG. 1.

TABLE 2

| Sample serial number | T (min) | A (Huperzine A) | W (ng) (Huperzine A) |
|---|---|---|---|
| 1 | 0 | 0 | 0 |
| 2 | 5 | 0 | 0 |
| 3 | 15 | 1479 | 1.397 |
| 4 | 35 | 2282 | 2.097 |
| 5 | 50 | 4699 | 4.202 |
| 6 | 65 | 5377 | 4.793 |
| 7 | 80 | 55654 | 5.034 |
| 8 | 95 | 6454 | 5.731 |
| 9 | 110 | 6456 | 5.731 |
| 10 | 140 | 8063 | 7.133 |
| 11 | 170 | 10696 | 9.426 |
| 12 | 200 | 10683 | 9.415 |
| 13 | 230 | 10706 | 9.435 |

Example 30

Analgesic effect of intragastric administration on mice measured with hot-plate test Materials 1) Animals Female ICR mice, weight 20+2 g, were purchased from Department of Laboratory Animal Science, Beijing University, animal license number: SCXK 2002-0001.

2) Drugs

A) Samples: samples were prepared as mixtures with 0.9% NaCl solution for intragastric administration to mice.

B) Fortanodyn: 30 mg/pill (TianJin LiSheng Pharmaceutical Co. Ltd, lot number: 0201001), 1.5 mg/mL solution was prepared with 0.9% NaCl solution for intragastric administration to mice.

Experimental Method

1) Hot-plate test on mice was employed. A thermostatic water bath was adjusted at 55±0.5° C., the bottom of metal plates contacted water surface and used as stimuli after heating. The time span(s) from the point when the mouse was placed onto the hot-plate to the time when the mouse started to lick its metapedes was determined as its pain threshold, which was recorded by stopwatch. Female mice with a weight of 20±2 g were used. The pain threshold of every mouse was measured twice before administration, and the qualified mice are the ones whose average pain threshold was less than 30 seconds.

The qualified mice were randomly grouped with 10 mice in each group. The pain threshold before administration was determined as the basic pain threshold. To the medication administration team, drugs of different dose were given through intragastric administration, whereas to the control group, 0.9% NaCl solution was given. The administration volume was 0.2 mL for every 10 g body weight. The pain threshold of each group was measured at 1 hour after administration. The results are shown in Table 3.

TABLE 3

The influence of tested compounds on pain-threshold of mice (1 hour) determined with hot-plate test ($x \pm s$, $n = 10$)

| Group | dosage (mg/kg) | pain threshold before administration (s) | pain threshold after administration (s) |
|---|---|---|---|
| Control | — | 12.4 ± 3.07 | 13.8 ± 2.48 |
| Fortanodyn | 30 | 12.6 ± 3.72 | 21.6 ± 1.85 |
| Example 4 | 0.6 | 12.2 ± 3.31 | 27.0 ± 5.40 |
| Example 8 | 0.6 | 12.8 ± 3.76 | 23.0 ± 3.52 |
| Example 10 | 0.6 | 11.8 ± 3.54 | 21.0 ± 3.16 |
| Example 12 | 0.6 | 12.4 ± 2.58 | 19.6 ± 4.03 |
| Example 15 | 0.6 | 13.0 ± 3.63 | 28.8 ± 3.92 |
| Example 16 | 0.6 | 13.2 ± 3.76 | 27.4 ± 5.16 |
| Example 18 | 0.6 | 13.0 ± 3.03 | 26.0 ± 5.01 |
| Example 20 | 0.6 | 12.6 ± 2.42 | 25.0 ± 5.18 |
| Example 24 | 0.6 | 12.2 ± 2.32 | 18.8 ± 3.31 |
| Example 26 | 0.6 | 12.8 ± 3.49 | 20.8 ± 3.60 |
| Aspirin | 100 | 12.4 ± 2.58 | 18.2 ± 3.71 |
| Example 5 | 0.6 | 12.8 ± 3.12 | 27.6 ± 6.22 |
| Example 7 | 0.6 | 12.4 ± 2.33 | 24.6 ± 5.61 |
| Example 9 | 0.6 | 12.4 ± 2.58 | 25.8 ± 4.35 |
| Example 11 | 0.6 | 12.8 ± 3.12 | 23.0 ± 4.98 |
| Example 13 | 0.6 | 12.4 ± 3.01 | 22.0 ± 4.86 |
| Example 17 | 0.6 | 12.2 ± 2.14 | 24.6 ± 5.46 |
| Example 19 | 0.6 | 12.0 ± 2.53 | 18.6 ± 3.44 |
| Example 22 | 0.6 | 12.4 ± 4.13 | 23.6 ± 4.27 |
| Example 27 | 0.6 | 12.4 ± 3.14 | 21.2 ± 5.53 |
| Example 28 | 0.6 | 12.6 ± 2.73 | 23.4 ± 3.88 |

After administration the pain threshold of each group at different time was measured. The results are shown in Table 4 and Table 5. The experimental data was statistically treated with t-test using SPSS10 statistics software.

TABLE 4

The influence of tested compounds on hot-plate pain-threshold of mice (x ± s, n = 10)

| Group | Dosage mg/kg | pain-threshold before administration (s) | pain-threshold at different time after administration(s) | | | | |
|---|---|---|---|---|---|---|---|
| | | | 30 min | 60 min | 120 min | 180 min | 240 min |
| Control | — | 11.7 ± 2.26 | 13.3 ± 1.95 | 14.6 ± 4.35 | 16.4 ± 4.48 | 15.7 ± 6.49 | 17.3 ± 3.80 |
| Example 2 | 0.73 | 13.2 ± 3.22 | 34.0 ± 11.42*** | 36.5 ± 10.91*** | 29.0 ± 7.83** | 24.0 ± 5.44** | 18.3 ± 5.31 |
| Example 3 | 0.76 | 12.9 ± 4.75 | 29.4 ± 9.16*** | 34.6 ± 7.50*** | 23.5 ± 7.28** | 24.8 ± 11.02** | 19.2 ± 5.59* |
| Example 6 | 0.76 | 11.6 ± 4.14 | 24.8 ± 8.77*** | 31.9 ± 7.76*** | 22.6 ± 8.37* | 25.9 ± 11.50* | 24.5 ± 10.55 |
| Example 14 | 0.81 | 12.6 ± 4.25 | 47.9 ± 12.95*** | 45.9 ± 15.42*** | 31.0 ± 12.04** | 25.1 ± 8.10** | 26.2 ± 9.69** |
| Example 21 | 0.71 | 11.9 ± 3.90 | 17.2 ± 6.37* | 21.0 ± 8.77** | 16.9 ± 8.32* | 12.9 ± 3.87 | |
| Example 23 | 0.84 | 12.3 ± 3.86 | 23.3 ± 7.45*** | 28.1 ± 10.15*** | 14.9 ± 5.02 | 13.7 ± 2.98 | |
| Example 25 | 0.82 | 12.6 ± 3.50 | 14.7 ± 3.62 | 17.5 ± 6.62* | 16.6 ± 5.91* | 13.4 ± 4.67 | |
| Aspirin | 100 | 12.4 ± 3.86 | 18.1 ± 5.40* | 18.0 ± 3.80* | 14.0 ± 3.63 | 14.3 ± 3.62 | |

Note:
compared with control group p < 0.05*;
p < 0.01**;
p < 0.001***

TABLE 5

Dose-effect relationship of the influence of tested compounds on hot-plate pain threshold of mice (x ± s, n = 10)

| Group | dosage mg/kg | pain threshold before administration (s) | pain threshold at different time after administration(s) | | | | |
|---|---|---|---|---|---|---|---|
| | | | 30 min | 60 min | 120 min | 180 min | 240 min |
| Control | — | 11.7 ± 2.26 | 13.3 ± 1.95 | 14.6 ± 4.35 | 16.4 ± 4.48 | 15.7 ± 6.49 | 17.3 ± 3.80 |
| Example 3 | 0.38 | 12.9 ± 3.38 | 16.7 ± 2.79* | 22.4 ± 5.19** | 17.6 ± 6.02* | 19.3 ± 6.16** | 20.0 ± 5.01** |
| Example 3 | 0.76 | 12.9 ± 4.75 | 29.4 ± 9.16*** | 34.6 ± 7.50*** | 23.5 ± 7.28** | 24.8 ± 11.02** | 19.2 ± 5.59** |
| Example 21 | 0.42 | 12.5 ± 2.79 | 16.3 ± 4.47* | 16.4 ± 4.03* | 13.2 ± 2.86 | 14.1 ± 1.66 | |
| Example 21 | 0.84 | 12.3 ± 3.86 | 23.3 ± 7.45*** | 28.1 ± 10.15*** | 14.9 ± 5.02 | 13.7 ± 2.98 | |

Note:
compared with the control group p < 0.05*;
p < 0.01**;
p < 0.001***

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. A compound of Formula I

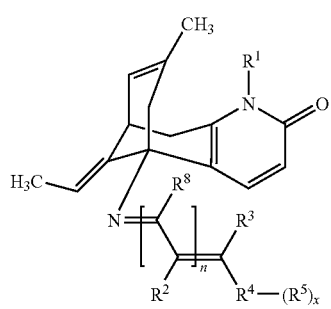

I or a pharmaceutically-acceptable salt thereof, wherein
$R^1$ is H, or $C_{1-4}$ alkyl;
$R^2$ is H, halogen, or $C_{1-4}$ alkyl;
$R^3$ is H, halogen, or $C_{1-4}$ alkyl, and $R^4$ is $C_{1-6}$ alkyl, aryl; or $=CR^3R^4$ is cyclopentylidene, cyclohexylidene, 1-methylpiperidin-4-ylidene, or inden-1-ylidene;
$R^5$ is independently at each occurrence F, Cl, Br, $CF_3$, $R^9$, $OR^9$, $NR^9R^{10}$, $NO_2$, CN, $COOR^9$, $O_2CR^3$, $CONR^9R^{10}$, $NR^9C(O)R^{10}$, heterocyclic group, aryl, or a group of Formula II

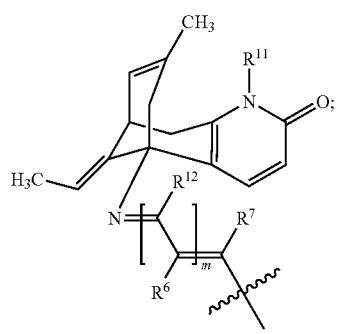

II $R^6$ is H, halogen, or $C_{1-4}$ alkyl
$R^7$ is H, halogen, or $C_{1-4}$ alkyl;
$R^8$ is H, $C_{1-4}$ alkyl group;
$R^9$ is H, or $C_{1-6}$ alkyl;
$R^{10}$ is H, or $C_{1-6}$ alkyl;
$R^{11}$ is H, or $C_{1-4}$ alkyl;
$R^{12}$ is H, or $C_{1-4}$ alkyl;
m is 0, 1, or 2;
when $R^5$ is F, Cl, Br, $CF_3$, $R^9$, $OR^9$, $NR^9R^{10}$, $NO_2$, CN, $COOR^9$, $O_2CR^9$, $CONR^9R^{10}$, $NR^9C(O)R^{10}$, heterocyclic group, or aryl, n is 1, 2, 3, or 4; when $R^5$ is the group of Formula II, n is 0, 1, 2, 3, or 4;
x is 0, 1, 2, 3, or 4.

2. The compound of claim 1, wherein $R^1$ is H.
3. The compound of claim 1, wherein $R^2$ is H, F, Cl, Br, or methyl.
4. The compound of claim 1, wherein $R^3$ is H, F, or methyl.
5. The compound of claim 1, wherein aryl is selected from phenyl, naphthalenyl, anthracenyl, pyridinyl, furanyl, indolyl, thienyl, or pyrrolyl.
6. The compound of claim 1, wherein $=CR^4R^3$ is cyclopentylidene, cyclohexylidene, 1-methylpiperidin-4-ylidene, or inden-1-ylidene.
7. The compound of claim 1, wherein
$R^5$ is F, Cl, $CF_3$, methyl, ethyl, propyl, OH, methoxyl, ethoxyl, propoxyl, $NH_2$, methylamino, ethylamino, propylamino, dimethylamino, diethylamino, dipropylamino, $NO_2$, CN, COOMe, COOEt, $O_2CMe$, $CONH_2$, $CONHMe$, $CONMe_2$, NHC(O)Me, NHC(O)H, N(Me)C(O)Me, N(Me)C(O)H, $O_2CH$, COOH; and x is 0, 1, 2, 3, or 4; n is 1, 2, 3, or 4.
8. The compound of claim 1, wherein
$R^5$ is a group of Formula II,

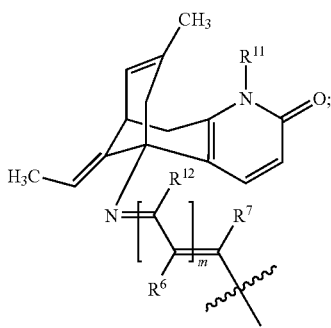

II $R^6$ is H or methyl;
$R^7$ is H or methyl;
$R^1$ and $R^{12}$ are independently H; and
m is 0, 1, or 2.

9. The compound of claim 1, selected from
1) (5R,9R,11E)-5-(3-phenylprop-2-en-1-ylideneamino)-11-ethylidene-5,6,9,10-tetrahydro-7-methyl-5,9-methylenecycloocta[b]pyridin-2(H)-one;
2) (5R,9R,11E)-5-(3-(4-methylphenyl)prop-2-en-1-ylideneamino)-11-ethylidene-5,6,9,10-tetrahydro-7-methyl-5,9-methanocycloocta[b]pyridin-2(H)-one;
3) (5R,9R,11E)-5-(3-(2-methylphenyl)prop-2-en-1-ylideneamino)-11-ethylidene-5,6,9,10-tetrahydro-7-methyl-5,9-methanocycloocta[b]pyridin-2(H)-one;
4) (5R,9R,11E)-5-(3-(3-methylphenyl)prop-2-en-1-ylideneamino)-11-ethylidene-5,6,9,10-tetrahydro-7-methyl-5,9-methanocycloocta[b]pyridin-2(H)-one;
5) (5R,9R,11E)-5-(3-(4-methoxylphenyl)prop-2-en-1-ylideneamino)-11-ethylidene-5,6,9,10-tetrahydro-7-methyl-5,9-methanocycloocta[b]pyridin-2(H)-one;
6) (5R,9R,11E)-5-(3-(2-methoxylphenyl)prop-2-en-1-ylideneamino)-11-ethylidene-5,6,9,10-tetrahydro-7-methyl-5,9-methanocycloocta[b]pyridin-2(H)-one;
7) (5R,9R,11E)-5-(3-(3-methoxylphenyl)prop-2-en-1-ylideneamino)-11-ethylidene-5,6,9,10-tetrahydro-7-methyl-5,9-methanocycloocta[b]pyridin-2(H)-one;
8) (5R,9R,11E)-5-(3-(2-chlorophenyl)prop-2-en-1-ylideneamino)-11-ethylidene-5,6,9,10-tetrahydro-7-methyl-5,9-methanocycloocta[b]pyridin-2(H)-one;
9) (5R,9R,11E)-5-(3-(3-chlorophenyl)prop-2-en-1-ylideneamino)-11-ethylidene-5,6,9,10-tetrahydro-7-methyl-5,9-methanocycloocta[b]pyridin-2(H)-one;
10) (5R,9R,11E)-5-(3-(4-chlorophenyl)prop-2-en-1-ylideneamino)-11-ethylidene-5,6,9,10-tetrahydro-7-methyl-5,9-methanocycloocta[b]pyridin-2(1H)-one;
11) (5R,9R,11E)-5-(3-(2-bromophenyl)prop-2-en-1-ylideneamino)-11-ethylidene-5,6,9,10-tetrahydro-7-methyl-5,9-methanocycloocta[b]pyridin-2(1H)-one;
12) (5R,9R,11E)-5-(3-(3-bromophenyl)prop-2-en-1-ylideneamino)-11-ethylidene-5,6,9,10-tetrahydro-7-methyl-5,9-methanocycloocta[b]pyridin-2(1H)-one;
13) (5R,9R,11E)-5-(3-(4-bromophenyl)prop-2-en-1-ylideneamino)-11-ethylidene-5,6,9,10-tetrahydro-7-methyl-5,9-methanocycloocta[b]pyridin-2(1H)-one;
14) (5R,9R,11E)-5-(3-(2-ethylphenyl)prop-2-en-1-ylideneamino)-11-ethylidene-5,6,9,10-tetrahydro-7-methyl-5,9-methanocycloocta[b]pyridin-2(1H)-one;
15) (5R,9R,11E)-5-(3-(3-ethylphenyl)prop-2-en-1-ylideneamino)-11-ethylidene-5,6,9,10-tetrahydro-7-methyl-5,9-methanocycloocta[b]pyridin-2(1H)-one;
16) (5R,9R,11E)-5-(3-(4-ethylphenyl)prop-2-en-1-ylideneamino)-11-ethylidene-5,6,9,10-tetrahydro-7-methyl-5,9-methanocycloocta[b]pyridin-2(1H)-one;
17) (5R,9R,11E)-5-(3-(2-propylphenyl)prop-2-en-1-ylideneamino)-11-ethylidene-5,6,9,10-tetrahydro-7-methyl-5,9-methanocycloocta[b]pyridin-2(1H)-one;
18) (5R,9R,11E)-5-(3-(3-propylphenyl)prop-2-en-1-ylideneamino)-11-ethylidene-5,6,9,10-tetrahydro-7-methyl-5,9-methanocycloocta[b]pyridin-2(1H)-one;
19) (5R,9R,11E)-5-(3-(4-propylphenyl)prop-2-en-1-ylideneamino)-11-ethylidene-5,6,9,10-tetrahydro-7-methyl-5,9-methanocycloocta[b]pyridin-2(1H)-one;
20) (5R,9R,11E)-5-(3-(2-isopropylphenyl)prop-2-en-1-ylideneamino)-11-ethylidene-5,6,9,10-tetrahydro-7-methyl-5,9-methanocycloocta[b]pyridin-2(1H)-one;
21) (5R,9R,11E)-5-(3-(3-isopropylphenyl)prop-2-en-1-ylideneamino)-11-ethylidene-5,6,9,10-tetrahydro-7-methyl-5,9-methanocycloocta[b]pyridin-2(1H)-one;
22) (5R,9R,11E)-5-(3-(4-isopropylphenyl)prop-2-en-1-ylideneamino)-11-ethylidene-5,6,9,10-tetrahydro-7-methyl-5,9-methanocycloocta[b]pyridin-2(1H)-one;
23) (5R,9R,11E)-5-(3-(naphthalen-2-yl)prop-2-en-1-ylideneamino)-11-ethylidene-5,6,9,10-tetrahydro-7-methyl-5,9-methanocycloocta[b]pyridin-2(1H)-one;
24) (5R,9R,11E)-5-(3-(naphthalen-1-yl)prop-2-en-1-ylideneamino)-11-ethylidene-5,6,9,10-tetrahydro-7-methyl-5,9-methanocycloocta[b]pyridin-2(1H)-one;
25) (5R,9R,11E)-5-(3-(furan-2-yl)prop-2-en-1-ylideneamino)-11-ethylidene-5,6,9,10-tetrahydro-7-methyl-5,9-methanocycloocta[b]pyridin-2(1H)-one;
26) (5R,9R,11E)-5-(3-(2-dimethylaminophenyl)prop-2-en-1-ylideneamino)-11-ethylidene-5,6,9,10-tetrahydro-7-methyl-5,9-methanocycloocta[b]pyridin-2(1H)-one;

27) (5R,9R,11E)-5-(3-(3-dimethylaminophenyl)prop-2-en-1-ylideneamino)-11-ethylidene-5,6,9,10-tetrahydro-7-methyl-5,9-methanocycloocta[b]pyridin-2(1H)-one;

28) (5R,9R,11E)-5-(3-(4-dimethylaminophenyl)prop-2-en-1-ylideneamino)-11-ethylidene-5,6,9,10-tetrahydro-7-methyl-5,9-methanocycloocta[b]pyridin-2(1H)-one;

29) (5R,9R,11E)-5-(3-(3,4-dimethoxylphenyl)prop-2-en-1-ylideneamino)-1-ethylidene-5,6,9,10-tetrahydro-7-methyl-5,9-methanocycloocta[b]pyridin-2(1H)-one;

30) (5R,9R,11E)-5-(3-(1H-indol-3-yl)prop-2-en-1-ylideneamino)-11-ethylidene-5,6,9,10-tetrahydro-7-methyl-5,9-methanocycloocta[b]pyridin-2(H)-one;

31) (5R,9R,11E)-5-(3-(pyridin-4-yl)prop-2-en-1-ylideneamino)-11-ethylidene-5,6,9,10-tetrahydro-7-methyl-5,9-methanocycloocta[b]pyridin-2(H)-one;

32) (5R,9R,11E)-5-(3-(pyridin-2-yl)prop-2-en-1-ylideneamino)-11-ethylidene-5,6,9,10-tetrahydro-7-methyl-5,9-methanocycloocta[b]pyridin-2(H)-one;

33) (5R,9R,11E)-5-(3-(pyridin-3-yl)prop-2-en-1-ylideneamino)-11-ethylidene-5,6,9,10-tetrahydro-7-methyl-5,9-methanocycloocta[b]pyridin-2(H)-one;

34) (5R,9R,11E)-5-(3-(thiophen-2-yl)prop-2-en-1-ylideneamino)-11-ethylidene-5,6,9,10-tetrahydro-7-methyl-5,9-methanocycloocta[b]pyridin-2(H)-one;

35) (5R,9R,11E)-5-(3-2-(methoxycarbonyl)phenyl)prop-2-en-1-ylideneamino)-11-ethylidene-5,6,9,10-tetrahydro-7-methyl-5,9-methanocycloocta[b]pyridin-2(1H)-one;

36) (5R,9R,11E)-5-(3-3-(methoxycarbonyl)phenyl)prop-2-en-1-ylideneamino)-11-ethylidene-5,6,9,10-tetrahydro-7-methyl-5,9-methanocycloocta[b]pyridin-2(1H)-one;

37) (5R,9R,11E)-5-(3-4-(methoxycarbonyl)phenyl)prop-2-en-1-ylideneamino)-11-ethylidene-5,6,9,10-tetrahydro-7-methyl-5,9-methanocycloocta[b]pyridin-2(1H)-one;

38) (5R,9R,11E)-5-(3-2-(ethoxycarbonyl)phenyl)prop-2-en-1-ylideneamino)-11-ethylidene-5,6,9,10-tetrahydro-7-methyl-5,9-methanocycloocta[b]pyridin-2(1H)-one;

39) (5R,9R,11E)-5-(3-3-(ethoxycarbonyl)phenyl)prop-2-en-1-ylideneamino)-11-ethylidene-5,6,9,10-tetrahydro-7-methyl-5,9-methanocycloocta[b]pyridin-2(1H)-one;

40) (5R,9R,11E)-5-(3-4-(ethoxycarbonyl)phenyl)prop-2-en-1-ylideneamino)-11-ethylidene-5,6,9,10-tetrahydro-7-methyl-5,9-methanocycloocta[b]pyridin-2(1H)-one;

41) (5R,9R,11E)-5-(3-2-(methylaminocarbonyl)phenyl)prop-2-en-1-ylideneamino)-11-ethylidene-5,6,9,10-tetrahydro-7-methyl-5,9-methanocycloocta[b]pyridin-2(1H)-one;

42) (5R,9R,11E)-5-(3-3-(methylaminocarbonyl)phenyl)prop-2-en-1-ylideneamino)-11-ethylidene-5,6,9,10-tetrahydro-7-methyl-5,9-methanocycloocta[b]pyridin-2(1H)-one;

43) (5R,9R,11E)-5-(3-4-(methylaminocarbonyl)phenyl)prop-2-en-1-ylideneamino)-11-ethylidene-5,6,9,10-tetrahydro-7-methyl-5,9-methanocycloocta[b]pyridin-2(1H)-one;

44) (5R,9R,11E)-5-(3-2-(dimethylaminocarbonyl)phenyl)prop-2-en-1-ylideneamino)-11-ethylidene-5,6,9,10-tetrahydro-7-methyl-5,9-methanocycloocta[b]pyridin-2(1H)-one;

45) (5R,9R,11E)-5-(3-3-(dimethylaminocarbonyl)phenyl)prop-2-en-1-ylideneamino)-11-ethylidene-5,6,9,10-tetrahydro-7-methyl-5,9-methanocycloocta[b]pyridin-2(1H)-one;

46) (5R,9R,11E)-5-(3-4-(dimethylaminocarbonyl)phenyl)prop-2-en-1-ylideneamino)-11-ethylidene-5,6,9,10-tetrahydro-7-methyl-5,9-methanocycloocta[b]pyridin-2(1H)-one; 47) (5R,9R,11E)-5-(3-2-(propoxycarbonyl)phenyl)prop-2-en-1-ylideneamino)-11-ethylidene-5,6,9,10-tetrahydro-7-methyl-5,9-methanocycloocta[b]pyridin-2(1H)-one;

48) (5R,9R,11E)-5-(3-3-(propoxycarbonyl)phenyl)prop-2-en-1-ylideneamino)-11-ethylidene-5,6,9,10-tetrahydro-7-methyl-5,9-methanocycloocta[b]pyridin-2(1H)-one;

49) (5R,9R,11E)-5-(3-4-(propoxycarbonyl)phenyl)prop-2-en-1-ylideneamino)-11-ethylidene-5,6,9,10-tetrahydro-7-methyl-5,9-methanocycloocta[b]pyridin-2(1H)-one;

50) (5R,9R,11E)-5-(3-2-(isopropoxycarbonyl)phenyl)prop-2-en-1-ylideneamino)-11-ethylidene-5,6,9,10-tetrahydro-7-methyl-5,9-methanocycloocta[b]pyridin-2(1H)-one;

51) (5R,9R,11E)-5-(3-3-(isopropoxycarbonyl)phenyl)prop-2-en-1-ylideneamino)-11-ethylidene-5,6,9,10-tetrahydro-7-methyl-5,9-methanocycloocta[b]pyridin-2(1H)-one;

52) (5R,9R,11E)-5-(3-4-(isopropoxycarbonyl)phenyl)prop-2-en-1-ylideneamino)-11-ethylidene-5,6,9,10-tetrahydro-7-methyl-5,9-methanocycloocta[b]pyridin-2(1H)-one;

53) (5R,9R,11E)-5-(3-2-(ethylaminocarbonyl)phenyl)prop-2-en-1-ylideneamino)-11-ethylidene-5,6,9,10-tetrahydro-7-methyl-5,9-methanocycloocta[b]pyridin-2(1H)-one;

54) (5R,9R,11E)-5-(3-3-(ethylaminocarbonyl)phenyl)prop-2-en-1-ylideneamino)-11-ethylidene-5,6,9,10-tetrahydro-7-methyl-5,9-methanocycloocta[b]pyridin-2(1H)-one;

55) (5R,9R,11E)-5-(3-4-(ethylaminocarbonyl)phenyl)prop-2-en-1-ylideneamino)-11-ethylidene-5,6,9,10-tetrahydro-7-methyl-5,9-methanocycloocta[b]pyridin-2(1H)-one;

56) (5R,9R,11E)-5-(3-(2-fluorophenyl)prop-2-en-1-ylideneamino)-11-ethylidene-5,6,9,10-tetrahydro-7-methyl-5,9-methanocycloocta[b]pyridin-2(H)-one;

57) (5R,9R,11E)-5-(3-(3-fluorophenyl)prop-2-en-1-ylideneamino)-11-ethylidene-5,6,9,10-tetrahydro-7-methyl-5,9-methanocycloocta[b]pyridin-2(H)-one;

58) (5R,9R,11E)-5-(3-(4-fluorophenyl)prop-2-en-1-ylideneamino)-11-ethylidene-5,6,9,10-tetrahydro-7-methyl-5,9-methanocycloocta[b]pyridin-2(H)-one;

59) (5R,9R,11E)-5-(3-(2-acetylaminophenyl)prop-2-en-1-ylideneamino)-1-ethylidene-5,6,9,10-tetrahydro-7-methyl-5,9-methanocycloocta[b]pyridin-2(1H)-one;

60) (5R,9R,11E)-5-(3-(3-acetylaminophenyl)prop-2-en-1-ylideneamino)-1-ethylidene-5,6,9,10-tetrahydro-7-methyl-5,9-methanocycloocta[b]pyridin-2(1H)-one;

61) (5R,9R,11E)-5-(3-(4-acetylaminophenyl)prop-2-en-1-ylideneamino)-1-ethylidene-5,6,9,10-tetrahydro-7-methyl-5,9-methanocycloocta[b]pyridin-2(1H)-one;

62) (5R,9R,11E)-5-(3-(2-diethylaminophenyl)prop-2-en-1-ylideneamino)-1-ethylidene-5,6,9,10-tetrahydro-7-methyl-5,9-methanocycloocta[b]pyridin-2(1H)-one;

63) (5R,9R,11E)-5-(3-(3-diethylaminophenyl)prop-2-en-1-ylideneamino)-1-ethylidene-5,6,9,10-tetrahydro-7-methyl-5,9-methanocycloocta[b]pyridin-2(1H)-one;

64) (5R,9R,11E)-5-(3-(4-diethylaminophenyl)prop-2-en-1-ylideneamino)-1-ethylidene-5,6,9,10-tetrahydro-7-methyl-5,9-methanocycloocta[b]pyridin-2(1H)-one;

65) (5R,9R,11E)-5-(3-(2-nitrophenyl)prop-2-en-1-ylideneamino)-11-ethylidene-5,6,9,10-tetrahydro-7-methyl-5,9-methanocycloocta[b]pyridin-2(H)-one;

66) (5R,9R,11E)-5-(3-(anthracen-9-yl)prop-2-en-1-ylideneamino)-11-ethylidene-5,6,9,10-tetrahydro-7-methyl-5,9-methanocycloocta[b]pyridin-2(H)-one;

67) (5R,9R,11E)-5-(3-methyl-3-phenylprop-2-en-1-ylideneamino)-11-ethylidene-5,6,9,10-tetrahydro-7-methyl-5,9-methanocycloocta[b]pyridin-2(H)-one;

68) (5R,9R,11E)-5-(2-methyl-3-phenylprop-2-en-1-ylideneamino)-11-ethylidene-5,6,9,10-tetrahydro-7-methyl-5,9-methanocycloocta[b]pyridin-2(H)-one;

69) (5R,9R,11E)-5-(2-chloro-3-phenylprop-2-en-1-ylideneamino)-11-ethylidene-5,6,9,10-tetrahydro-7-methyl-5,9-methanocycloocta[b]pyridin-2(H)-one;

70) (5R,9R,11E)-5-(3-chloro-3-phenylprop-2-en-1-ylideneamino)-11-ethylidene-5,6,9,10-tetrahydro-7-methyl-5,9-methanocycloocta[b]pyridin-2(H)-one;

71) (5R,9R,11E)-5-(5-phenylpent-2,4-dien-1-ylideneamino)-11-ethylidene-5,6,9,10-tetrahydro-7-methyl-5,9-methanocycloocta[b]pyridin-2(H)-one;

72) (5R,9R,11E)-5-(7-phenylhept-2,4,6-trien-1-ylideneamino)-11-ethylidene-5,6,9,10-tetrahydro-7-methyl-5,9-methanocycloocta[b]pyridin-2(H)-one; or 73) (5R,9R,11E)-5-(2-(indan-1-ylidene)-ethylideneamino)-11-ethylidene-5,6,9,10-tetrahydro-7-methyl-5,9-methanocycloocta[b]pyridin-2(H)-one.

10. A pharmaceutical preparation comprising a pharmaceutically-acceptable excipient and at least one compound of claim 1.

11. The pharmaceutical preparation of claim 10, wherein the pharmaceutically-acceptable excipient is a carrier material, a bulking agent, a solvent, a diluent, a colorant, or an adhesive.

12. The pharmaceutical preparation of claim 10, formulated for a mode of administration selected from gastrointestinal, oral, buccal, intravenous, abdominal, dermal, intramuscular, nasal, ocular, pulmonary, anal, vaginal, percutaneous, hypodermic, or transdermal.

13. A method for treating pain, functional pain syndrome or organic pain syndrome comprising administering to a patient in need thereof a compound of claim 1.

14. The method of claim 13, wherein pain, functional pain syndrome or organic pain syndrome are selected from: neuropathic headache, migraine, primary fibromyalgia, postoperative pain, visceral pain, toothache, neuralgia, courbature, arthralgia, menstrual pain, or pain resulting from amputation, tumoral denervation, traumatic denervation, nerve injury, inflammation, or autoimmune disorder.

15. The method of claim 13, wherein pain is migraine pain.

16. The method of claim 13, wherein the compound of claim 1 is administered to the patient at a dose of between 10 µg and 100 mg.

17. A method for preparing a compound of Formula I

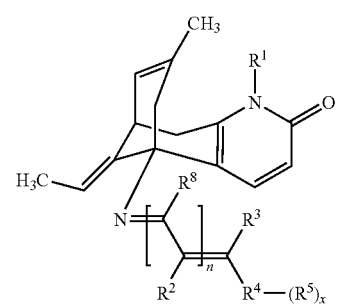

comprising the steps of:
(a) (i) contacting a compound of Formula III

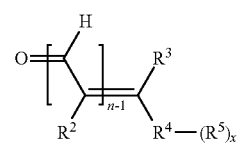

with malonic acid to yield a compound of Formula V

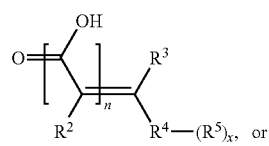

(ii) contacting a compound of Formula III with trimethyl phosphonoacetate to give a compound of Formula IV

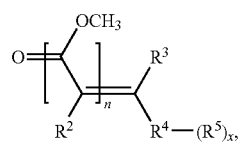

and hydrolyzing the compound of Formula IV to yield a compound of Formula V;

(b) contacting the compound of Formula V with carbonyldiimidazole to yield a corresponding acylated imidazole, and reducing the corresponding acylated imidazole to yield a compound of Formula VI

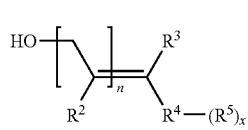

(c) oxidizing the compound of Formula VI to yield a compound of Formula VII

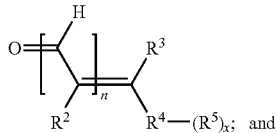
VII and (d) contacting the compound of Formula VII with a compound for Formula VIII

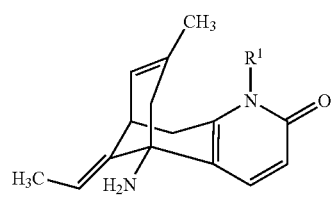
VIII to yield the compound of Formula I;
wherein
$R^1$ is H, or $C_{1-4}$ alkyl;
$R^2$ is H, halogen, or $C_{1-4}$ alkyl;
$R^3$ is H, halogen, or $C_{1-4}$ alkyl, and $R^4$ is $C_{1-6}$ alkyl, aryl; or $=CR^3R^4$ is cyclopentylidene, cyclohexylidene, 1-methylpiperidin-4-ylidene, or inden-1-ylidene;

$R^5$ is independently at each occurrence F, Cl, Br, $CF_3$, $R^9$, $OR^9$, $NR^9R^{10}$, $NO_2$, CN, $COOR^9$, $O_2CR^9$, $CONR^9R^{10}$, $NR^9C(O)R^{10}$, heterocyclic group, aryl, or a group of Formula II

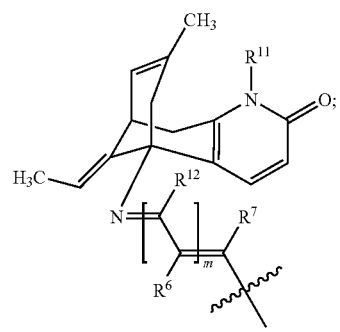
II $R^6$ is H, halogen, or $C_{1-4}$ alkyl;
$R^7$ is H, halogen, or $C_{1-4}$ alkyl;
$R^8$ is H, $C_{1-4}$ alkyl group;
$R^9$ is H, or $C_{1-6}$ alkyl;
$R^{10}$ is H, or $C_{1-6}$ alkyl;
$R^{11}$ is H, or $C_{1-4}$ alkyl;
$R^{12}$ is H, or $C_{1-4}$ alkyl;
m is 0, 1, or 2;
x is 0, 1, 2, 3, or 4; and
when $R^5$ is F, Cl, Br, $CF_3$, $R^9$, $OR^9$, $NR^9R^{10}$, $NO_2$, CN, $COOR^9$, $O_2CR^9$, $CONR^9R^{10}$, $NR^9C(O)R^{10}$, heterocyclic group, or aryl, n is 1, 2, 3, or 4; and when $R^5$ is the group of Formula II, n is 0, 1, 2, 3, or 4.

* * * * *